US012751685B2

(12) United States Patent
Takagi et al.

(10) Patent No.: US 12,751,685 B2
(45) Date of Patent: Oct. 6, 2026

(54) RADIOGRAPHIC IMAGING SUPPORT SYSTEM, RADIOGRAPHIC IMAGING SUPPORT METHOD, AND RECORDING MEDIUM

(71) Applicant: Konica Minolta, Inc., Tokyo (JP)

(72) Inventors: Tatsuya Takagi, Mitaka (JP); Atsushi Taneda, Koganei (JP); Kenichi Yanagisawa, Kokubunji (JP); Naoki Hayashi, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 272 days.

(21) Appl. No.: 18/464,569

(22) Filed: Sep. 11, 2023

(65) Prior Publication Data

US 2024/0090864 A1 Mar. 21, 2024

(30) Foreign Application Priority Data

Sep. 21, 2022 (JP) ................................ 2022-150422

(51) Int. Cl.
*A61B 6/00* (2024.01)
*A61B 6/46* (2024.01)

(52) U.S. Cl.
CPC .............. *A61B 6/547* (2013.01); *A61B 6/461* (2013.01)

(58) Field of Classification Search
CPC ....... G03B 17/561; G06T 1/20; G06T 7/0012; G06T 2207/30008; G06T 2207/10116; G06T 1/0007; G06T 7/0016; G06T 2207/10124; G06T 7/0002; G06T 7/001; G06T 2207/30168; G06T 2207/30004; A61B 6/469; A61B 6/4208; A61B 6/461; A61B 6/505; A61B 6/463; A61B 6/547;
(Continued)

(56) References Cited

U.S. PATENT DOCUMENTS

2022/0353409 A1* 11/2022 Ma ........................ H04N 23/695
2023/0267608 A1* 8/2023 Horiuchi .............. G03B 17/561
348/61
2024/0415476 A1* 12/2024 Sugahara .................. G06T 7/11

FOREIGN PATENT DOCUMENTS

CN 109381208 A 2/2019
JP 2017-536860 A 12/2017
(Continued)

OTHER PUBLICATIONS

Office Action, dated Dec. 16, 2025, which was issued for the corresponding Japanese Patent Application No. 2022-150422, with an English translation.
Office Action, dated Aug. 21, 2026, which was issued forthe corresponding Chinese Patent Application No. 202311198912.X., 16 pages, with English machine translation.

*Primary Examiner* — Irakli Kiknadze

(74) *Attorney, Agent, or Firm* — LUCAS & MERCANTI, LLP

(57) ABSTRACT

A radiographic imaging support system that supports positioning of a radiographing site of a subject with respect to a radiographic imaging apparatus, includes a hardware processor that acquires image information based on an optical image obtained by capturing an image of the radiographing site with an optical camera, generates first target position information regarding a target position of the radiographing site, and outputs the generated first target position information. The first target position information includes information corresponding to a size of the radiographing site.

11 Claims, 13 Drawing Sheets

(58) Field of Classification Search

CPC ....... A61B 6/08; A61B 6/4464; A61B 6/4452; A61B 6/4233; A61B 6/4291; A61B 6/465; A61B 6/5252; A61B 6/5258; A61B 6/5282; A61B 6/5294; A61B 6/54; A61B 6/542; A61B 6/545; A61B 6/464; A61B 6/4405; A61B 6/00; A61B 6/548; A61B 6/563; A61B 6/4266; A61B 6/5241; A61B 6/56; A61B 6/5235; A61B 6/4283; A61B 6/4494; A61B 6/566; A61B 6/467; A61B 6/022; A61B 6/502; A61B 6/587; A61B 6/58; A61B 6/40; A61B 6/4028; A61B 6/466; A61B 6/5247; A61B 6/46; A61B 6/52; H05G 1/44; H05G 1/60; H04N 25/78; H04N 23/661; H04N 25/75; H04N 5/32; G06F 19/321; G06Q 30/0601; G06Q 50/22; G16H 40/40

USPC .................................................... 378/205, 62

See application file for complete search history.

(56) References Cited

FOREIGN PATENT DOCUMENTS

| | | | |
|---|---|---|---|
| JP | 2019-33830 | A | 3/2019 |
| JP | 2019-097769 | A | 6/2019 |
| JP | 2021-137259 | A | 9/2021 |

* cited by examiner

RADIOGRAPHIC IMAGING SUPPORT SYSTEM, RADIOGRAPHIC IMAGING SUPPORT METHOD, AND RECORDING MEDIUM

CROSS-REFERENCE TO RELATED APPLICATIONS

The entire disclosure of Japanese Patent Application No. 2022-150422 filed on Sep. 21, 2022 is incorporated herein by reference in its entirety.

TECHNICAL FIELD

The present invention relates to a radiographic imaging support system, a radiographic imaging support method, and a recording medium.

DESCRIPTION OF THE RELATED ART

Conventionally, in the medical field, diagnosis has been performed on the basis of radiographs obtained through radiographic imaging.

To succeed in radiographic imaging, it is important to appropriately perform positioning of a patient (subject). To achieve this, a technique of supporting positioning of a patient in radiographic imaging is disclosed.

For example, JP 2019-97769 A describes a technique of supporting positioning of radiographic imaging this time using a radiograph of the same radiographing site as a radiographing site to be radiographed this time, which was radiographed in the past.

Further, JP 2017-536860 A describes the following technique. A virtual scene (initial target position) of a virtual patient at a correct position or in a correct pose stored in advance is subjected to registration with current spatial information of a radiographing site of an actual patient captured with an optical camera to generate a target position to be adapted. Then, an optical image of the actual patient obtained with the optical camera and the target position to be adapted of the virtual patient are displayed.

SUMMARY OF THE INVENTION

However, in the invention described in JP 2019-97769 A, a radiograph of the same patient radiographed in the past is required, and thus, there is a problem that the invention cannot be utilized for a patient for whom radiographic imaging is to be performed for the first time.

Further, in the invention described in JP 2017-536860 A, the target position to be adapted is merely based on a virtual scene of a virtual patient. Thus, in a case where a size of the target position to be adapted does not fit a size of the actual patient, and the size of the target position to be adapted is larger than the size of the actual patient, a gap occurs with respect to the target position to be adapted. Further, in an opposite case, the target position to be adapted is covered by the actual patient. In other words, there is a possibility that positioning cannot be easily performed at an appropriate position.

A problem to be solved by the present invention is to provide a radiographic imaging support system capable of easily positioning a subject at an appropriate radiographing position, a radiographic imaging support method, and a recording medium.

To achieve at least one of the abovementioned objects, according to an aspect of the present invention, a radiographic imaging support system reflecting one aspect of the present invention is a radiographic imaging support system that supports positioning of a radiographing site of a subject with respect to a radiographic imaging apparatus, the radiographic imaging support system including:

a hardware processor that acquires image information based on an optical image obtained by capturing an image of the radiographing site with an optical camera, generates first target position information regarding a target position of the radiographing site using the image information acquired as input using a learned classifier, and outputs the generated first target position information, in which the first target position information includes information corresponding to a size of the radiographing site.

To achieve at least one of the abovementioned objects, according to an aspect of the present invention, a radiographic imaging support system reflecting one aspect of the present invention is a radiographic imaging support system that supports positioning of a radiographing site of a subject with respect to the radiographic imaging apparatus, the radiographic imaging support system including:

a hardware processor that acquires image information based on an optical image obtained by capturing an image of the radiographing site with an optical camera, generates first target position information regarding a target position of the radiographing site on the basis of first reference position information regarding a radiographing position of the radiographing site and the image information acquired, and outputs the generated first target position information, in which the first target position information includes information corresponding to a size of the radiographing site.

To achieve at least one of the abovementioned objects, according to an aspect of the present invention, a radiographic imaging support method reflecting one aspect of the present invention is a radiographic imaging support method for supporting positioning of a radiographing site of a subject with respect to a radiographic imaging apparatus, the radiographic imaging support method including:

by a hardware processor, acquiring image information based on an optical image obtained by capturing an image of the radiographing site with an optical camera, generating first target position information regarding a target position of the radiographing site using the image information acquired as input using a learned classifier, and outputting the generated first target position information, in which the first target position information includes information corresponding to a size of the radiographing site.

To achieve at least one of the abovementioned objects, according to an aspect of the present invention, a radiographic imaging support method reflecting one aspect of the present invention is a radiographic imaging support method for supporting positioning a radiographing site of a subject with respect to a radiographic imaging apparatus, the radiographic imaging support method including:

by a hardware processor, acquiring image information based on an optical image obtained by capturing an image of the radiographing site with an optical camera, generating first target position information regarding a target position of the radiographing site on the basis of first reference position information regarding a radiographing position of the radiographing site and the image information acquired, and outputting the generated first target position information, in which the first target position information includes information corresponding to a size of the radiographing site.

To achieve at least one of the abovementioned objects, according to an aspect of the present invention, a recording medium reflecting one aspect of the present invention is a non-transitory computer-readable recording medium storing a program for causing a computer of a radiographic imaging support system that supports positioning of a radiographing site of a subject with respect to a radiographic imaging apparatus, to acquire image information based on an optical image obtained by capturing an image of the radiographing site with an optical camera, generate first target position information regarding a target position of the radiographing site using the image information acquired as input using a learned classifier, and output the generated first target position information, in which the first target position information includes information corresponding to a size of the radiographing site.

To achieve at least one of the abovementioned objects, according to an aspect of the present invention, a recording medium reflecting one aspect of the present invention is a non-transitory computer-readable recording medium storing a program for causing a computer of a radiographic imaging support system that supports positioning of a radiographing site of a subject with respect to a radiographic imaging apparatus, to acquire image information based on an optical image obtained by capturing an image of the radiographing site with an optical camera, generate first target position information regarding a target position of the radiographing site on the basis of first reference position information regarding a radiographing position of the radiographing site and the image information acquired, and output the generated first target position information, in which the first target position information includes information corresponding to a size of the radiographing site.

To achieve at least one of the abovementioned objects, according to an aspect of the present invention, a radiographic imaging support system reflecting one aspect of the present invention is a radiographic imaging support system that supports positioning of a radiographing site of a subject with respect to a radiographic imaging apparatus, the radiographic imaging support system including:

a hardware processor that acquires image information based on an optical image obtained by capturing an image of the radiographing site with an optical camera, generates second target position information regarding a target position of a related site corresponding to the radiographing site using the image information acquired as input using a learned classifier, and outputs the generated second target position information.

To achieve at least one of the abovementioned objects, according to an aspect of the present invention, a radiographic imaging support system reflecting one aspect of the present invention is a radiographic imaging support system that supports positioning of a radiographing site of a subject with respect to a radiographic imaging apparatus, the radiographic imaging support system including:

a hardware processor that acquires image information based on an optical image obtained by capturing an image of the radiographing site with an optical camera, generates second target position information regarding a target position of a related site corresponding to the radiographing site on the basis of second reference position information regarding a position of the related site corresponding to a radiographing position of the radiographing site and the image information acquired, and outputs the generated second target position information.

To achieve at least one of the abovementioned objects, according to an aspect of the present invention, a radiographic imaging support method reflecting one aspect of the present invention is a radiographic imaging support method for supporting positioning of a radiographing site of a subject with respect to a radiographic imaging apparatus, the radiographic imaging support method including:

by a hardware processor, acquiring image information based on an optical image obtained by capturing an image of the radiographing site with an optical camera, generating second target position information regarding a target position of a related site corresponding to the radiographing site using the image information acquired as input using a learned classifier, and outputting the generated second target position information.

To achieve at least one of the abovementioned objects, according to an aspect of the present invention, a radiographic imaging support method reflecting one aspect of the present invention is a radiographic imaging support method for supporting positioning of a radiographing site of a subject with respect to a radiographic imaging apparatus, the radiographic imaging support method including:

by a hardware processor, acquiring image information based on an optical image obtained by capturing an image of the radiographing site with an optical camera, generating second target position information regarding a target position of a related site corresponding to the radiographing site on the basis of second reference position information regarding a position of the related site corresponding to a radiographing position of the radiographing site and the image information acquired, and outputting the generated second target position information.

To achieve at least one of the abovementioned objects, according to an aspect of the present invention, a recording medium reflecting one aspect of the present invention is a non-transitory computer-readable recording medium storing a program for causing a computer of a radiographic imaging support system that supports positioning of a radiographing site of a subject with respect to a radiographic imaging apparatus, to acquire image information based on an optical image obtained by capturing an image of the radiographing site with an optical camera, generate second target position information regarding a target position of a related site corresponding to the radiographing site using the image information acquired as input using a learned classifier, and output the generated second target position information.

To achieve at least one of the abovementioned objects, according to an aspect of the present invention, a recording medium reflecting one aspect of the present invention is a non-transitory computer-readable recording medium storing a program for causing a computer of a radiographic imaging support system that supports positioning of a radiographing site of a subject with respect to a radiographic imaging apparatus, to acquire image information based on an optical image obtained by capturing an image of the radiographing site with an optical camera, generate second target position information regarding a target position of a related site corresponding to the radiographing site on the basis of second reference position information regarding a position of the related site corresponding to a radiographing position of the radiographing site and the image information acquired, and output the generated second target position information.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Hereinafter, one or more embodiments of the present invention will be described with reference to the drawings. However, the scope of the invention is not limited to the disclosed embodiments.

First Embodiment (Configuration of Radiographic Imaging Support System 100)

A configuration of a first embodiment of the present invention will be described first.

Figure 1:
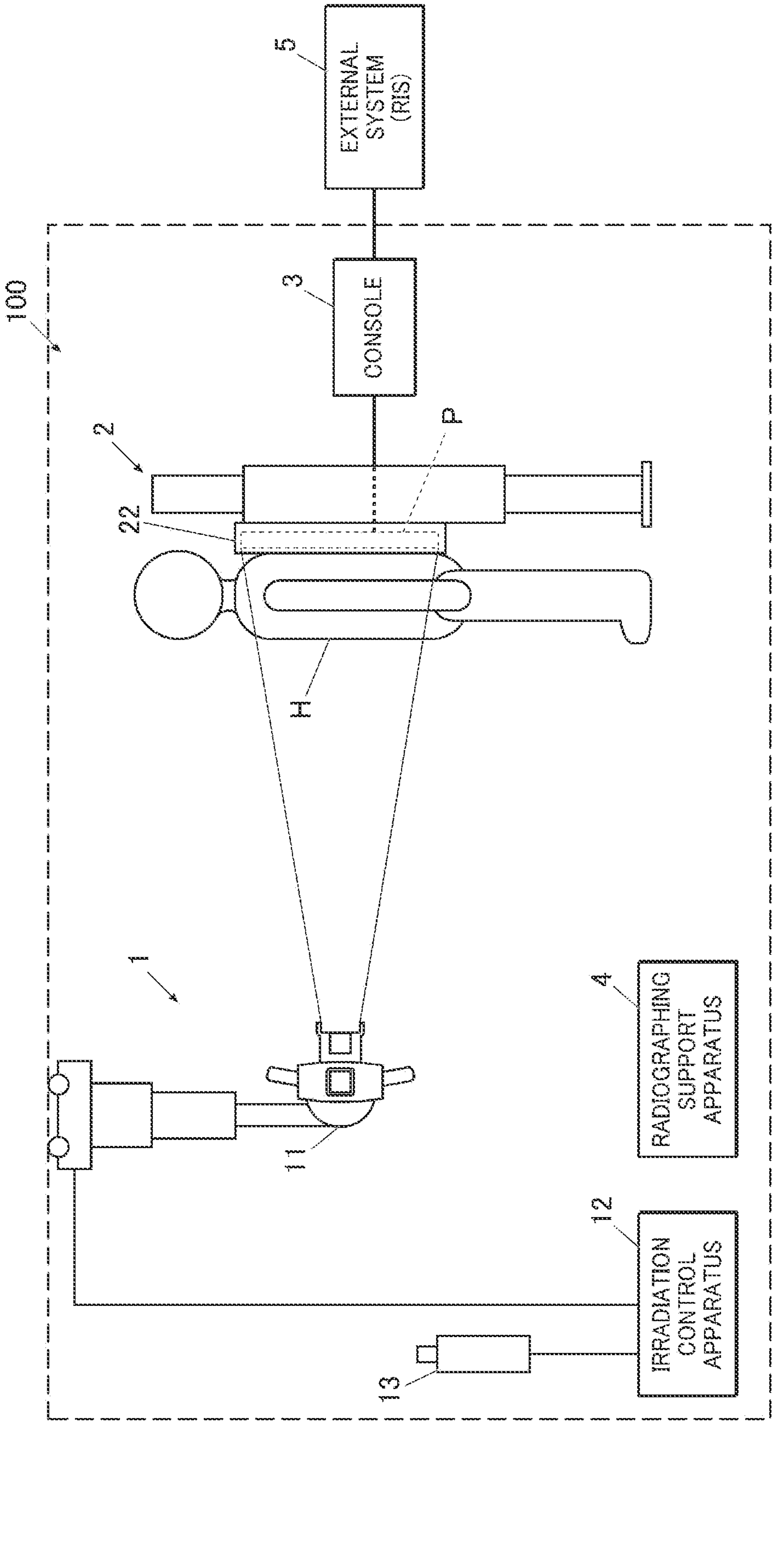
FIG. 1 is a view illustrating an overall configuration of a radiographic imaging support system in a first embodiment.

FIG. 1 is a view illustrating an example of an overall configuration of a radiographic imaging support system 100 according to the first embodiment of the present invention.

As illustrated in FIG. 1, the radiographic imaging support system 100 includes a radiation irradiation apparatus 1, a radiation detection apparatus 2, a console 3 and a radiographing support apparatus 4.

The console 3 is connected to the radiation detection apparatus 2 so as to be able to transmit/receive (transmit or receive) data.

Further, the radiation irradiation apparatus 1 and the radiation detection apparatus 2 constitute a radiographic imaging apparatus.

The radiation irradiation apparatus 1 includes a radiation source 11, an irradiation control apparatus 12 and an irradiation switch 13.

The radiation source 11 is disposed at a position facing the radiation detection apparatus 2 across a subject H and radiates radiation (X-ray) to the subject H.

The irradiation control apparatus 12 includes an operation interface that accepts input of radiation irradiation conditions, and the like. If the irradiation switch 13 is depressed by an operator of the radiation irradiation apparatus 1, the irradiation control apparatus 12 causes the radiation source 11 to radiate radiation on the basis of the input radiation irradiation conditions.

The radiation detection apparatus 2 detects radiation that is radiated from the radiation source 11 and passes through the subject H and captures a radiograph.

The radiation detection apparatus 2 includes a detector holder 22, a radiation detector P, and the like.

The radiation detector P includes a flat panel detector (FPD), and the like.

The radiation detector P includes, for example, a glass substrate, and the like, and detects radiation (X-rays) at a predetermined position on the substrate, which is radiated from the radiation irradiation apparatus 1 and passes through at least the subject H in accordance with intensity of the radiation. Then, a plurality of detection elements (pixels) that convert the detected radiation into electrical signals and accumulate the electrical signals are arranged in a matrix on the radiation detector P. Each pixel includes a switch such as, for example, a thin film transistor (TFT).

The radiation detector P controls the switch of each pixel on the basis of image reading conditions input from the console 3, switches reading of the electrical signals accumulated in each pixel and reads the electrical signals accumulated in each pixel, thereby acquires image data.

Then, the radiation detector P outputs the acquired image data to the console 3.

The console 3 outputs the image reading conditions to the radiation detector P to control radiograph reading operation by the radiation detector P.

Figure 2:
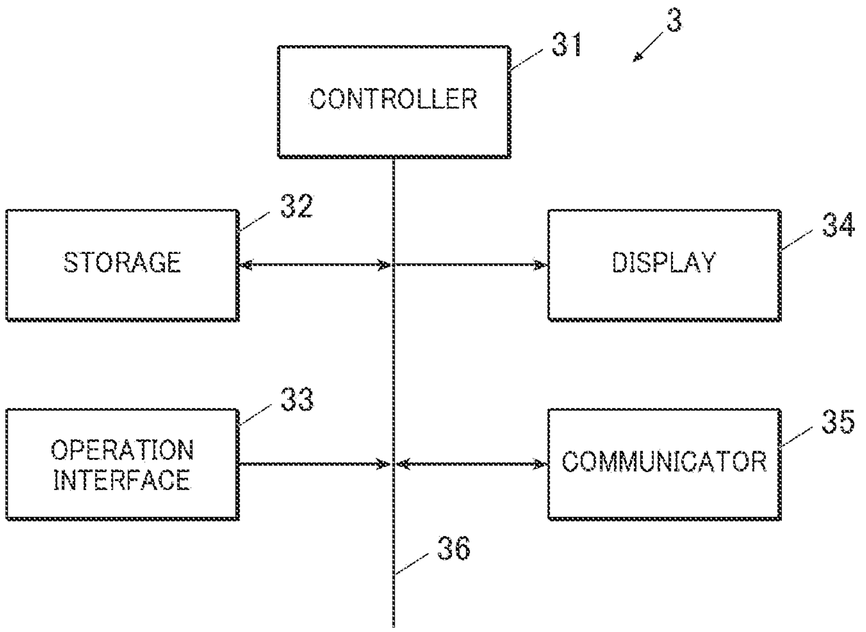
FIG. 2 is a block diagram illustrating a functional configuration of a console in FIG. 1.

As illustrated in FIG. 2, the console 3 includes a controller 31, a storage 32, an operation interface 33, a display 34 and a communicator 35, which are connected by a bus 36.

The controller 31 includes a central processing unit (CPU), a random access memory (RAM), and the like. The CPU of the controller 31 reads out and loads to the RAM, a system program and various kinds of processing programs stored in the storage 32 in accordance with operation of the operation interface 33 and performs centralized control on operation of respective components of the console 3 in accordance with the loaded programs.

The storage 32 includes a nonvolatile semiconductor memory, a hard disk, and the like. The storage 32 stores various kinds of programs to be executed by the controller 31, parameters necessary for processing by the programs or data such as processing results. Various kinds of programs are stored in a form of readable program codes, and the controller 31 sequentially executes operation in accordance with the program codes.

Further, the storage 32 stores a radiograph acquired through radiographic imaging in association with patient information (such as a patient ID and patient name) and examination information (such as examination date and radiographing conditions).

The operation interface 33, which includes a keyboard including a cursor key, number input keys, various kinds of function keys, and the like, and a pointing device such as a mouse, outputs an instruction signal input through key operation on the keyboard and mouse operation, to the controller 31. Further, the operation interface 33 may include a touch panel on a display screen of the display 34, in which case, the operation interface 33 outputs an instruction signal input via the touch panel to the controller 31.

The display 34, which includes a monitor such as a liquid crystal display (LCD) and a cathode ray tube (CRT), displays an input instruction, data, and the like, from the operation interface 33 in accordance with an instruction of a display signal input from the controller 31.

The communicator 35 includes an interface for transmitting/receiving data to/from (to or from) the radiation detection apparatus 2, and the like. Note that the console 3 and the radiation detection apparatus 2 may perform communication either in a wired manner or in a wireless manner.

Further, the communicator 35 is connected to an external system 5 via a network and can exchange order information, and the like.

The radiographing support apparatus 4 is an apparatus that supports positioning of a radiographing site of the subject H with respect to the radiographic imaging apparatus.

Figure 3:
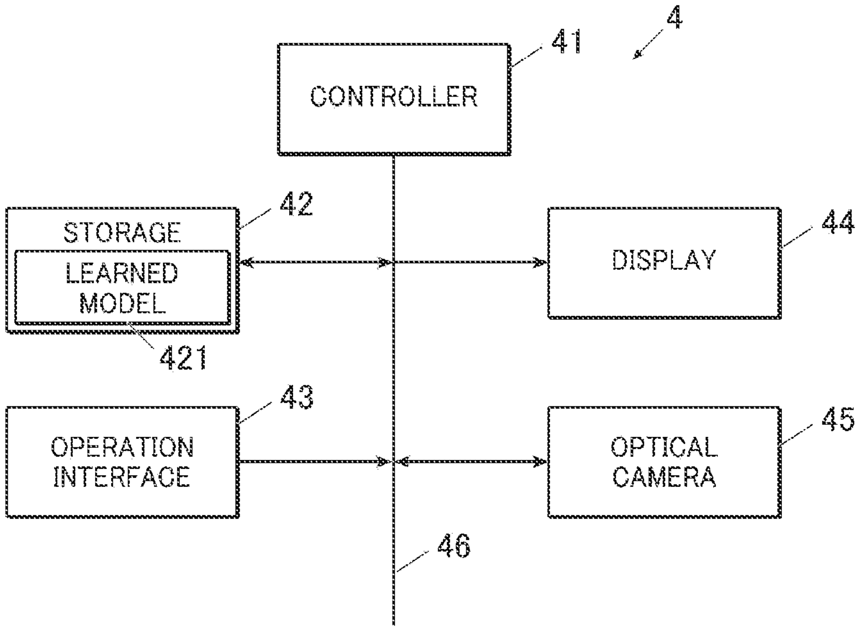
FIG. 3 is a block diagram illustrating a functional configuration of a radiographing support apparatus in FIG. 1.

As illustrated in FIG. 3, the radiographing support apparatus 4 includes a controller 41 (hardware processor), a storage 42, an operation interface 43, a display 44 and an optical camera 45, which are connected by a bus 46.

The controller 41 includes a CPU, a RAM, and the like. The CPU of the controller 41 reads out and loads to the RAM, a system program and various kinds of processing programs stored in the storage 42 and performs centralized control on operation of respective components of the radiographing support apparatus 4 in accordance with the loaded program.

The storage 42 includes a nonvolatile semiconductor memory, a hard disk, and the like.

The storage 42 stores various kinds of programs to be executed by the controller 41, parameters necessary for execution of processing by the programs or data such as processing results. Various kinds of programs are stored in a form of readable program codes, and the controller 41 sequentially executes operation in accordance with the program codes.

Further, the storage 42 stores a first threshold (predetermined first threshold) for each radiographing site to be used to determine whether first target position information matches first current position information on the basis of a difference between the first target position information and the first current position information in radiographing support processing which will be described later. The first threshold is, for example, set at a relatively small value in a case where the radiographing site is a fine site such as the finger and set at a relatively great value in a case where the radiographing site is a large site such as the knee.

Further, the storage 42 stores a learned model 421 to be used in the radiographing support processing.

The learned model 421 is a model that is caused to perform machine learning (deep learning) using image data of an optical image captured with the optical camera 45 and the first target position information (correct label) for each radiographing site corresponding to the image data. The first target position information is information regarding a target position that is a position appropriate for radiographic imaging of the radiographing site of the subject H.

Further, if the image data of the optical image is input, the learned model 421 performs inference and generates radiographing site information indicating the radiographing site at which radiographing is performed in the optical image, radiographing site region information indicating a region of the radiographing site and the first target position information of the radiographing site.

The learned model 421 may be artificial intelligence (AI) having a deep-learned neural network.

Further, the learned model 421 may be a model that is further caused to perform machine learning using information from an external apparatus capable of performing communication with the radiographing support apparatus 4. The information from the external apparatus includes, for example, patient information and medical care information from HIS/RIS, or the like, optical image data targeting at the whole patient or the whole radiographing room using an optical camera different from the optical camera 45, viewpoint information upon radiographing of a radiographer such as an eye tracker, examination information such as electrocardiogram and oxygen concentration used at the same time.

The operation interface 43, which includes a keyboard including a cursor key, number input keys, various kinds of function keys, and the like, and a pointing device such as a mouse, outputs an instruction signal input through key operation on the keyboard and mouse operation, to the controller 41. Further, the operation interface 43 may include a touch panel on a display screen of the display 44, in which case, the operation interface 43 outputs an instruction signal input via the touch panel to the controller 41.

The display 44, which includes a monitor such as an LCD and a CRT, displays data, and the like, in accordance with an instruction of a display signal input from the controller 41.

In the present embodiment, the display 44 is disposed at a position at which the operator (such as a radiographer) of the radiographic imaging apparatus and the subject H can visually confirm the display 44.

The optical camera 45, which includes, for example, a charge coupled device (CCD) camera, a complementary metal oxide semiconductor device (CMOS) camera, an infrared camera, and the like, captures an optical image.

In the present embodiment, the optical camera 45 acquires an optical image of a region (basically, a region irradiated with radiation or a region slightly larger than the region) including a region irradiated with radiation from the radiation source 11.

The optical camera 45 is, for example, provided in the vicinity of the radiation source 11 of the radiation irradiation apparatus 1. Note that the optical camera 45 can change a direction (imaging direction).

The optical camera 45 captures an optical image in accordance with an instruction from the controller 41 and transmits the captured optical image to the controller 41.

Note that the radiographing support apparatus 4 may include a plurality of optical cameras 45.

The external system 5 is an external information system coordinating with the console 3, and in the present embodiment, for example, a radiology information systems (RIS).

(Operation of Radiographic Imaging Support System 100)

Operation of the radiographic imaging support system 100 will be described next.

Figure 4:
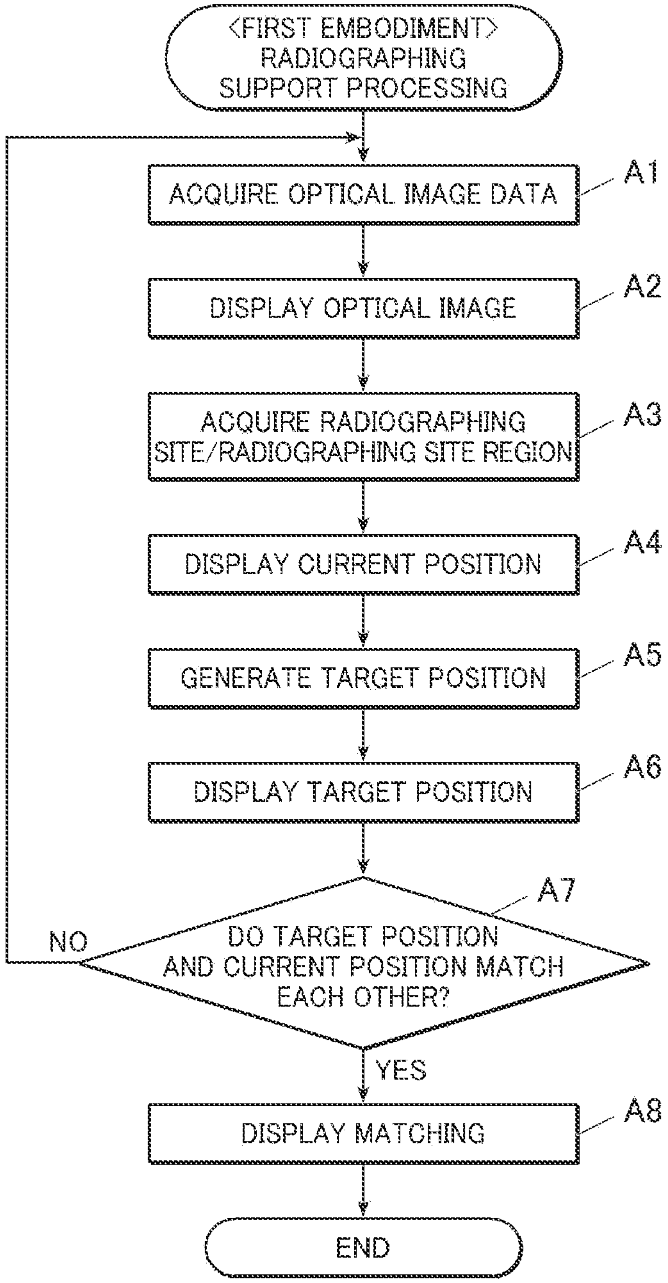
FIG. 4 is a flowchart indicating flow of radiographing support processing in the first embodiment.

FIG. 4 is a flowchart indicating radiographing support processing to be executed by the radiographing support apparatus 4. The radiographing support processing is executed by cooperation of the controller 41 and the program stored in the storage 42 before radiographic imaging.

First, the controller 41 causes the optical camera 45 to capture the radiographing site of the subject H and acquires image data of the optical image (image information based on the optical image) (step A1). In other words, the controller 41 acquires image information based on the optical image obtained by capturing the radiographing site of the subject with the optical camera 45. Here, the controller 41 functions as an acquirer. The step A1 is an acquisition process.

For example, the operator positions the subject H and gives an instruction to perform imaging with the optical camera 45 using the operation interface 43. The controller 41 causes the optical camera 45 to perform imaging in response to the imaging instruction by the operation interface 43. Then, the optical camera 45 captures an optical image in an imaging direction set in advance and transmits the optical image to the controller 41. This enables the controller 41 to acquire an optical image of a region including a region to be irradiated with radiation from the radiation source 11, for example, a region to be irradiated with radiation from the radiation source 11 or a region slightly larger than the region.

Then, the controller 41 displays the optical image acquired in step A1 on the display 44 (step A2).

Then, the controller 41 recognizes the radiographing site of the subject and the radiographing site region on the basis of the image data of the optical image acquired in step A1 (step A3).

Specifically, the controller 41 inputs the image data of the optical image acquired in step A1 to the learned model 421. Then, the controller 41 acquires the radiographing site information of the subject H and the radiographing site region information as output of the learned model 421.

Then, the controller 41 displays an outline of the radiographing site region acquired in step A3 as an outline of a current position of the radiographing site in a superimposed manner on the optical image displayed in step A2 (step A4). The outline of the current position of the radiographing site indicates a size of the radiographing site.

Here, the outline indicates a contour (of the radiographing site of the subject H). However, if a shape and a size of the outline can be displayed in a recognizable manner, the controller 41 may display only part of the contour of the radiographing site. For example, in a case where the radiographing site is a foot, the controller 41 displays only an inner contour and an outer contour of the foot.

Figure 5:
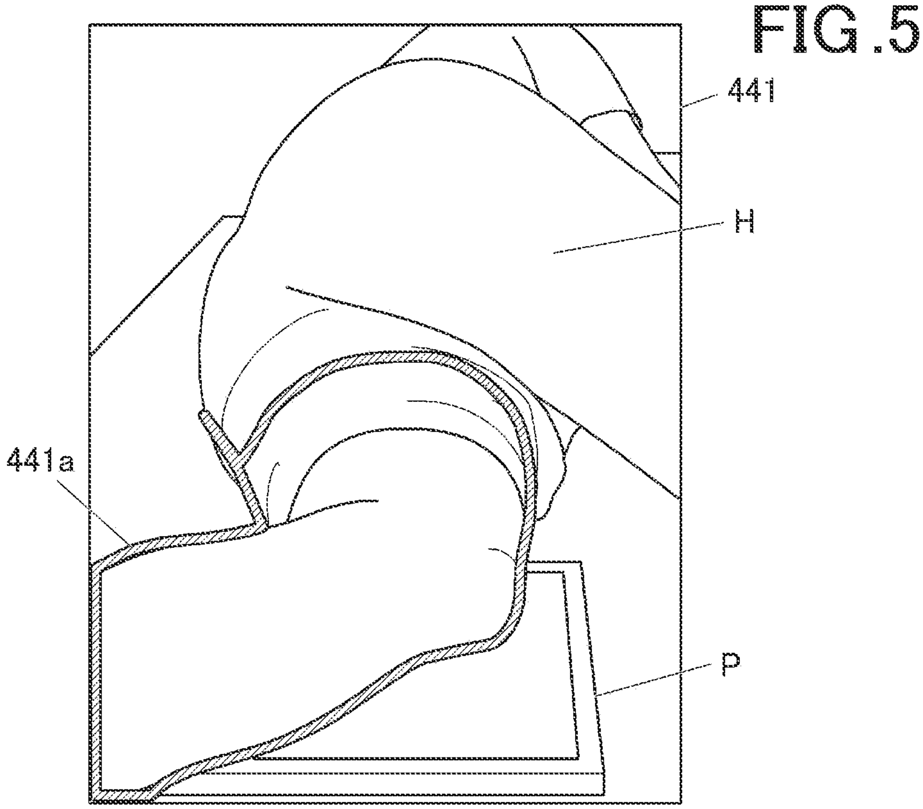
FIG. 5 is a view illustrating an example where an outline of a current position of a radiographing site is displayed in a superimposed manner on an optical image.

FIG. 5 is a view illustrating an example where an outline 441*a* of the current position of the radiographing site is displayed in a superimposed manner on the optical image 441.

Then, the controller 41 acquires first target position information corresponding to the radiographing site information acquired in step A3 as output of the learned model 421. Further, the controller 41 corrects the first target position information on the basis of the outline of the current position of the radiographing site and the imaging direction of the optical camera 45 to generate the first target position information corresponding to the size of the radiographing site (step A5). In other words, the controller 41 generates the first target position information regarding the target position of the radiographing site using the image information based on the optical image acquired by the acquirer as input using the learned model 421 (learned classifier). Here, the controller 41 functions as a generator. Further, the first target position information includes information corresponding to the size of the radiographing site (information corresponding to the outline of the current position of the radiographing site). Further, the first target position information is based on the imaging direction of the optical camera 45. The step A5 is a generation process.

Then, the controller 41 displays the first target position information corresponding to the size of the radiographing site generated in step A5 as the outline of the target position of the radiographing site in a superimposed manner on the optical image displayed in step A2 (step A6). In other words, the controller 41 outputs the first target position information generated by the generator. Here, the controller 41 functions as an output device. The step A6 is an output process.

Figure 6:
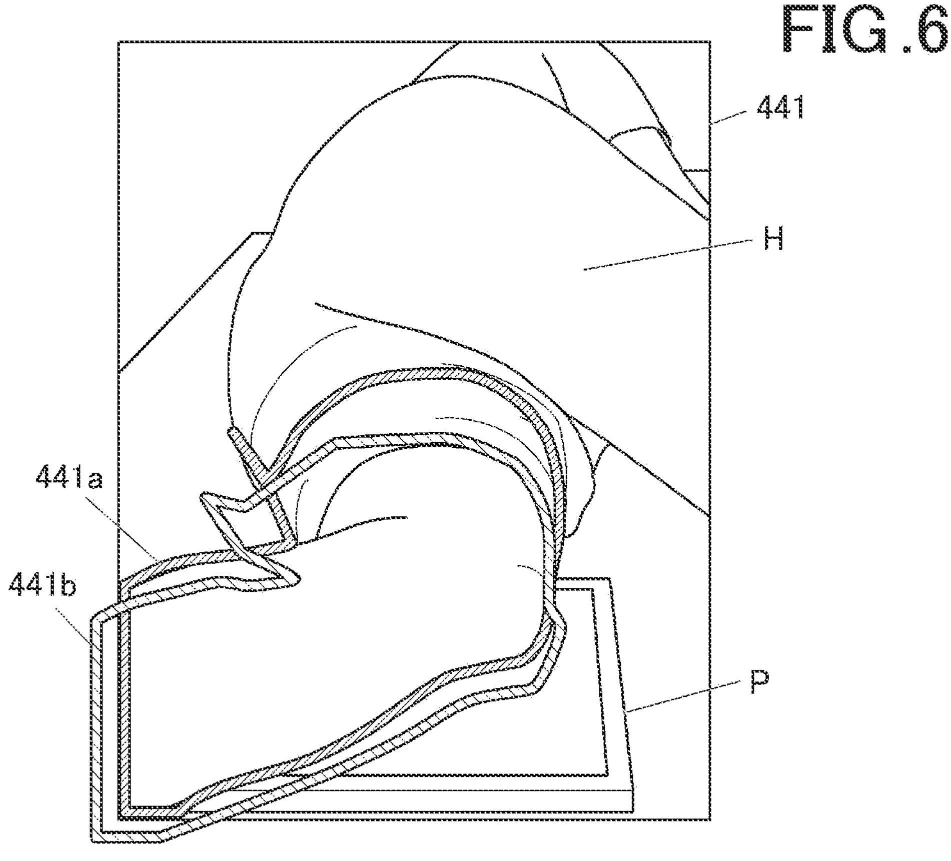
FIG. 6 is a view illustrating an example where the outline of the current position of the radiographing site and an outline of a target position of the radiographing site are displayed in a superimposed manner on the optical image.

FIG. 6 is a view illustrating an example where the outline 441*a* of the current position of the radiographing site and an outline 441*b* of the target position of the radiographing site are displayed in a superimposed manner on the optical image 441.

Note that the controller 41 displays the outline 441*b* of the target position of the radiographing site so that the outline 441*b* is located on at least part of the radiation detector P as illustrated in FIG. 6 when the outline 441*b* of the target position of the radiographing site is displayed. In other words, the controller 41 outputs the optical image including the radiation detector P of the radiation detection apparatus 2 provided in the radiographic imaging apparatus and outputs the optical image so that the first target position information is located on at least part of the radiation detector P of the radiation detection apparatus 2 in the optical image.

Further, as illustrated in FIG. 6, the controller 41 displays the outline 441*a* of the current position of the radiographing site and the outline 441*b* of the target position of the radiographing site with different colors. In other words, the controller 41 outputs the outline 441*b* of the target position of the radiographing site (first target position information) and the outline 441*a* of the current position of the radiographing site (the first current position information regarding the radiographing site included in the image information) in a distinguishable form. Note that the distinguishable form is not limited to a difference in color and may be a difference in type or thickness of lines of the outlines, blinking of the lines of the outlines, provision of symbols or characters, and the like.

Then, the controller 41 determines whether or not the outline of the current position of the radiographing site displayed in step A4 matches the outline of the target position of the radiographing site displayed in step A6 (step A7).

Specifically, the controller 41 acquires a first threshold corresponding to the radiographing site information acquired from the storage 42 in step A3. Then, in a case where a difference between the outline of the current position of the radiographing site and the outline of the target position of the radiographing site is within the first threshold, the controller 41 determines that the outline of the current position of the radiographing site matches the outline of the target position of the radiographing site. In other words, in a case where a difference between the first target position information and the first current position information is within a predetermined first threshold, the controller 41 determines that the first target position information matches the first current position information. Here, the controller 41 functions as a determiner.

In a case where the outline of the current position of the radiographing site matches the outline of the target position of the radiographing site (step A7: YES), the controller 41 displays matching in a distinguishable form (step A8), and ends the present processing. In other words, in a case where it is determined by the determiner that the first target position information matches the first current position information, the controller 41 outputs matching in a distinguishable form.

Figure 7:
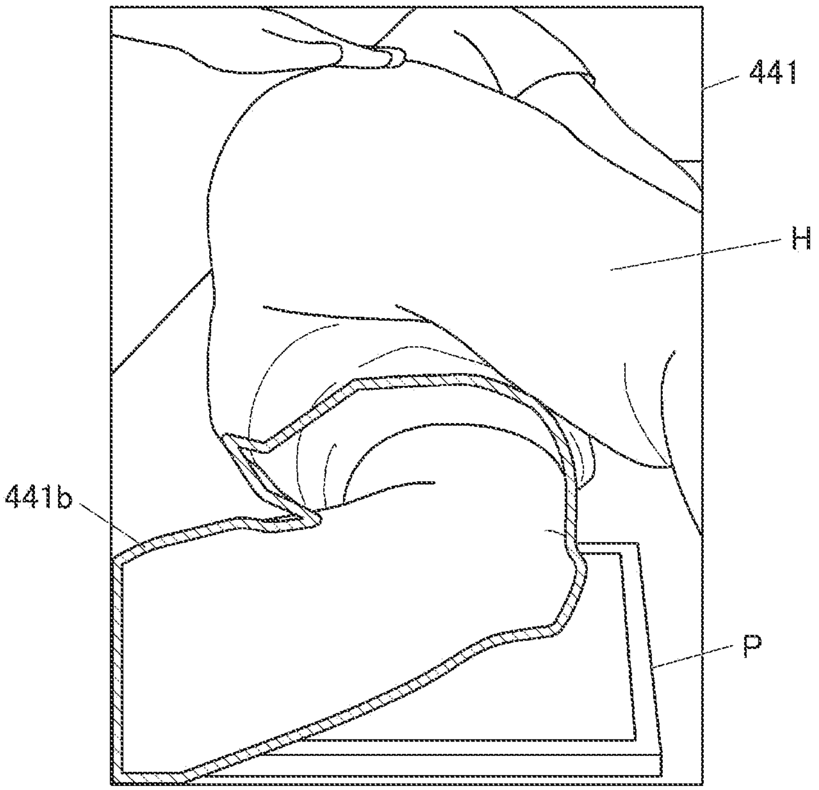
FIG. 7 is a view illustrating an example where matching of target position information and current position information is displayed in a distinguishable form.

FIG. 7 illustrates an example where matching of the outline of the current position of the radiographing site and the outline of the target position of the radiographing site is displayed in a distinguishable form.

In the example illustrated in FIG. 7, in a case where the outline 441*a* of the current position of the radiographing site matches (overlaps) the outline 441*b* of the target position of the radiographing site, the controller 41 deletes the outline 441*a* of the current position of the radiographing site and displays only the outline 441*b* of the target position of the radiographing site. Note that in this case, the controller 41 may display the outline 441*b* of the target position of the radiographing site after matching with a color different from a color of the outline 441*b* of the target position of the radiographing site before matching or the outline 441*a* of the current position of the radiographing site.

This enables the operator or the subject H to recognize that the current position of the radiographing site matches a position (target position) appropriate for radiographic imaging.

When the operator recognizes that the current position of the radiographing site matches the position appropriate for radiographic imaging, the operator starts radiographic imaging in the radiographic imaging apparatus.

On the other hand, in a case where the outline of the current position of the radiographing site does not match the outline of the target position of the radiographing site (step A7; NO), the controller 41 returns the present processing to step A1. Then, the controller 41 repeatedly performs the processing from step A1 to step A7 until the outlines match each other.

The operator or the subject H moves the radiographing site so that the outline 441*a* of the current position of the radiographing site displayed on the display 44 matches the outline 441*b* of the target position of the radiographing site.

Second Embodiment

A second embodiment of the present invention will be described next. Points different from the first embodiment will be mainly described below.

Figure 8:
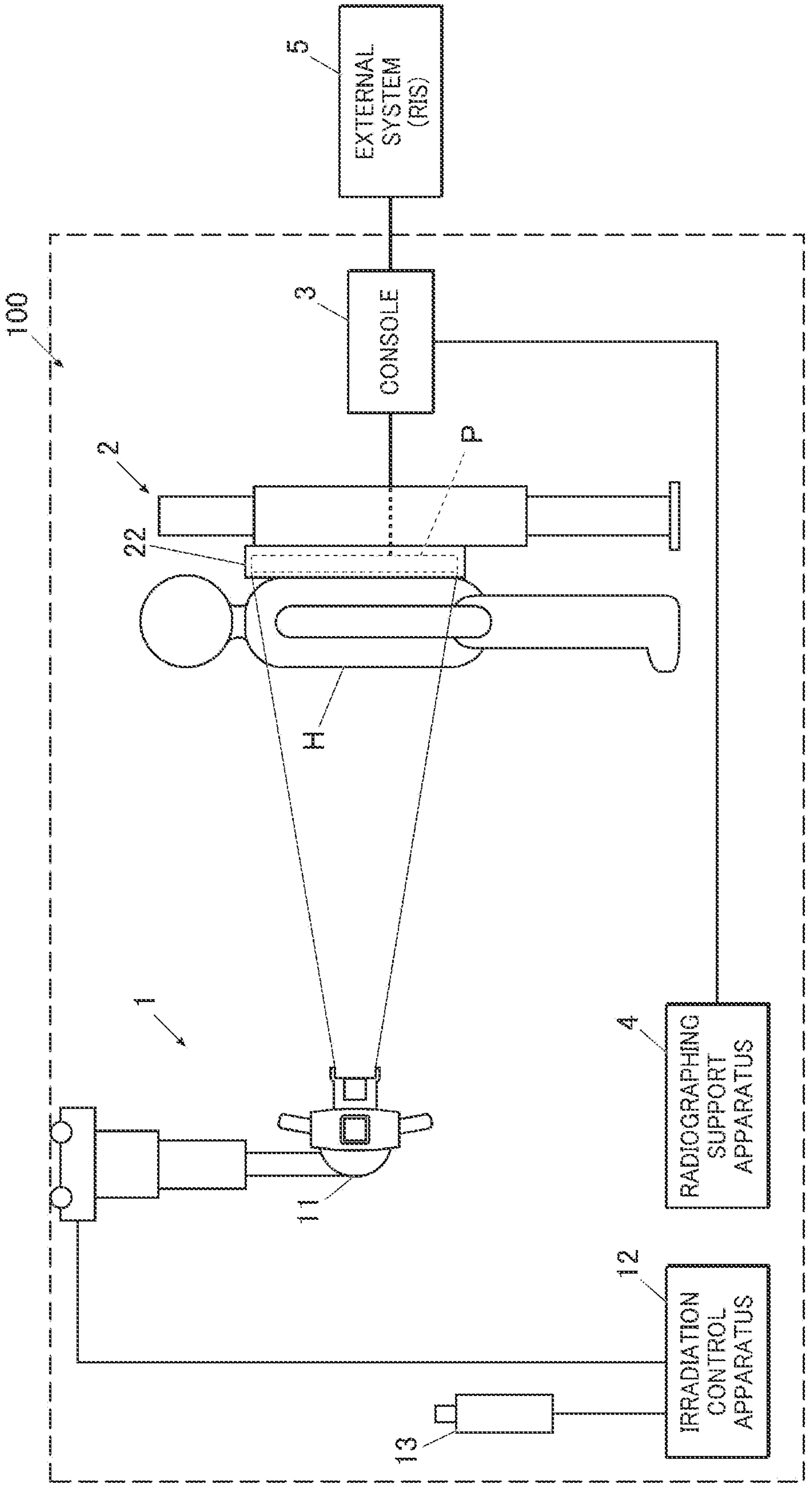
FIG. 8 is a view illustrating an overall configuration of a radiographic imaging support system in a second embodiment.

FIG. 8 illustrates a configuration of the radiographic imaging support system 100 of the second embodiment.

As illustrated in FIG. 8, in the second embodiment, the console 3 is connected to the radiation detection apparatus 2 and the radiographing support apparatus 4 so as to be able to transmit/receive data.

Further, the storage 42 in the second embodiment stores a template image for each radiographing site.

Further, the storage 42 stores first reference position information indicating a reference position regarding a radiographic imaging position for each radiographing site.

Figure 9:
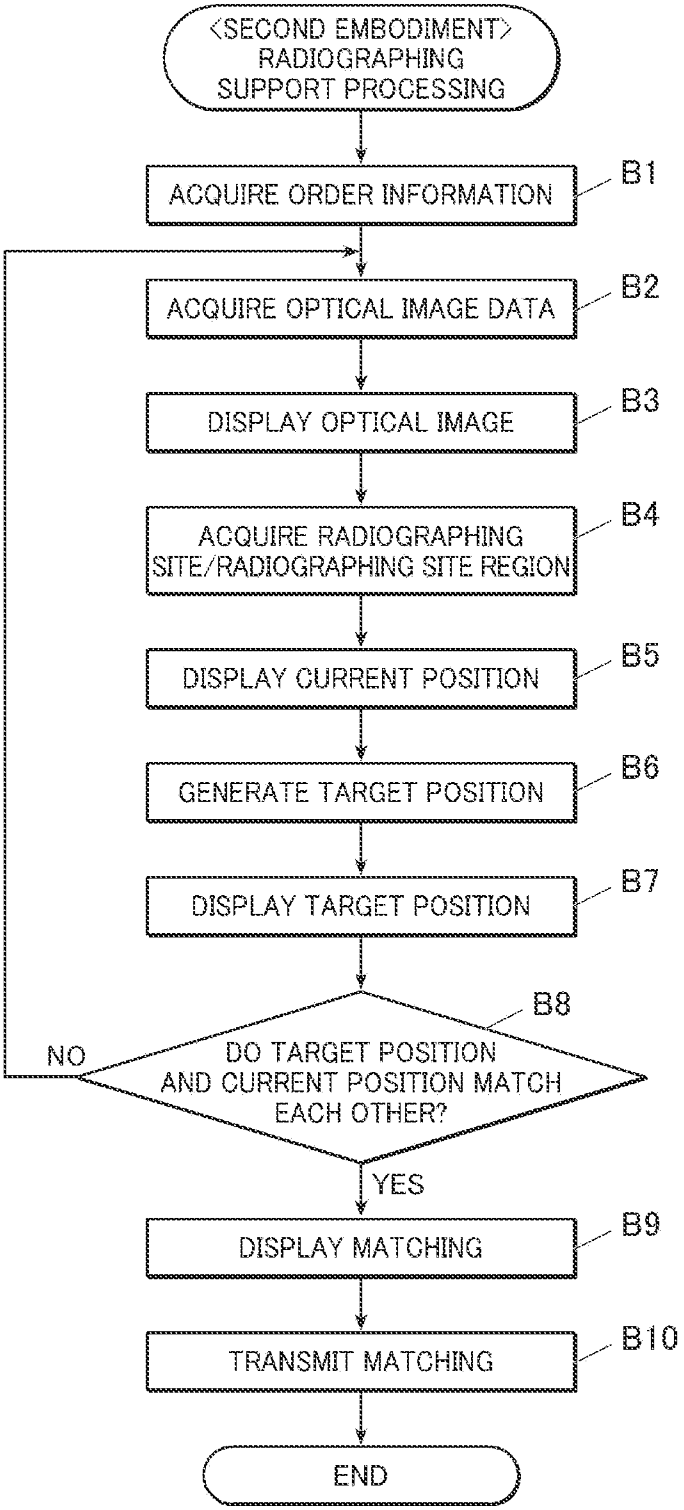
FIG. 9 is a flowchart indicating flow of radiographing support processing in the second embodiment.

FIG. 9 indicates a flowchart of radiographing support processing in the second embodiment.

First, the controller 41 acquires order information transmitted from the external system 5 to the console 3, from the console 3 (step B1).

The order information includes patient information of a patient who is a subject, radiographing conditions, examination items, request information, and the like. The radiographing conditions include posture information upon radiographing, an irradiation direction, information on a radiographing site (such as, for example, breast and leg), a tube voltage and a tube current, an irradiation period, a body type of the patient, whether or not there is a grid, and the like. Note that the radiographing site also includes a radiographing direction such as front, side and oblique directions.

Then, the controller 41 performs processing in steps B2 and B3 that is similar to the processing in steps A1 and A2 of the above-described radiographing support processing.

Then, the controller 41 acquires radiographing site information of the subject from the order information acquired in step B1.

Then, the controller 41 acquires a template image corresponding to the radiographing site information acquired from the order information, from the storage 42.

Then, the controller 41 recognizes (acquires) the radiographing site region in the image data of the optical image acquired in step B2 by performing template matching using the template image (step B4).

Then, the controller 41 performs processing in step B5 that is similar to the processing in step A4 of the above-described radiographing support processing.

Then, the controller 41 acquires the first reference position information corresponding to the radiographing site information acquired in step B4, from the storage 42.

Then, the controller 41 generates first target position information corresponding to a size of the radiographing site by correcting the first reference position information on the basis of the outline of the current position of the radiographing site and the imaging direction of the optical camera 45 (step B6). In other words, the controller 41 generates the first target position information regarding the target position of the radiographing site on the basis of the first reference position information regarding the radiographing position of the radiographing site and the image information acquired by the acquirer. Here, the controller 41 functions as a generator. Further, the first target position information includes information corresponding to the size of the radiographing site (information corresponding to the outline of the radiographing site). Further, the first target position information is based on the imaging direction of the optical camera 45. The step B6 is a generation process.

Then, the controller 41 displays the first target position information corresponding to the size of the radiographing site generated in step B6 as the outline of the target position of the radiographing site in a superimposed manner on the optical image displayed in step B3 (step B7). In other words, the controller 41 outputs the first target position information generated by the generator. Here, the controller 41 functions as an output device. The step B7 is an output process.

Then, the controller 41 performs processing in steps B8 and B9 that is similar to the processing in steps A7 and A8 of the above-described radiographing support processing.

After step B9, the controller 41 transmits a notification indicating that the current position of the radiographing site matches the position appropriate for radiographic imaging to the console 3 (step B10), and the present processing ends.

When the console 3 receives the notification indicating that the current position of the radiographing site matches the position appropriate for radiographic imaging from the radiographing support apparatus 4, the console 3 starts radiographic imaging through instruction operation by the operator.

Note that the controller 41 may transmit data for display for displaying a fact that the outline of the current position of the radiographing site matches the outline of the target position of the radiographing site in a distinguishable form, to the console 3 in step B10. When the console 3 receives the data for display, the console 3 performs display on the display 34 on the basis of the data for display.

On the other hand, in a case where the outline of the current position of the radiographing site does not match the outline of the target position of the radiographing site (step B8; NO), the controller 41 returns the present processing to step B2. Then, the controller 41 repeatedly performs the processing from step B2 to step B8 until the outlines match each other.

The operator or the subject H moves the radiographing site so that the outline 441*a* of the current position of the radiographing site displayed on the display 44 matches the outline 441*b* of the target position of the radiographing site.

Third Embodiment

A third embodiment of the present invention will be described next. Points different from the first embodiment and the second embodiment will be mainly described below.

Figure 10:
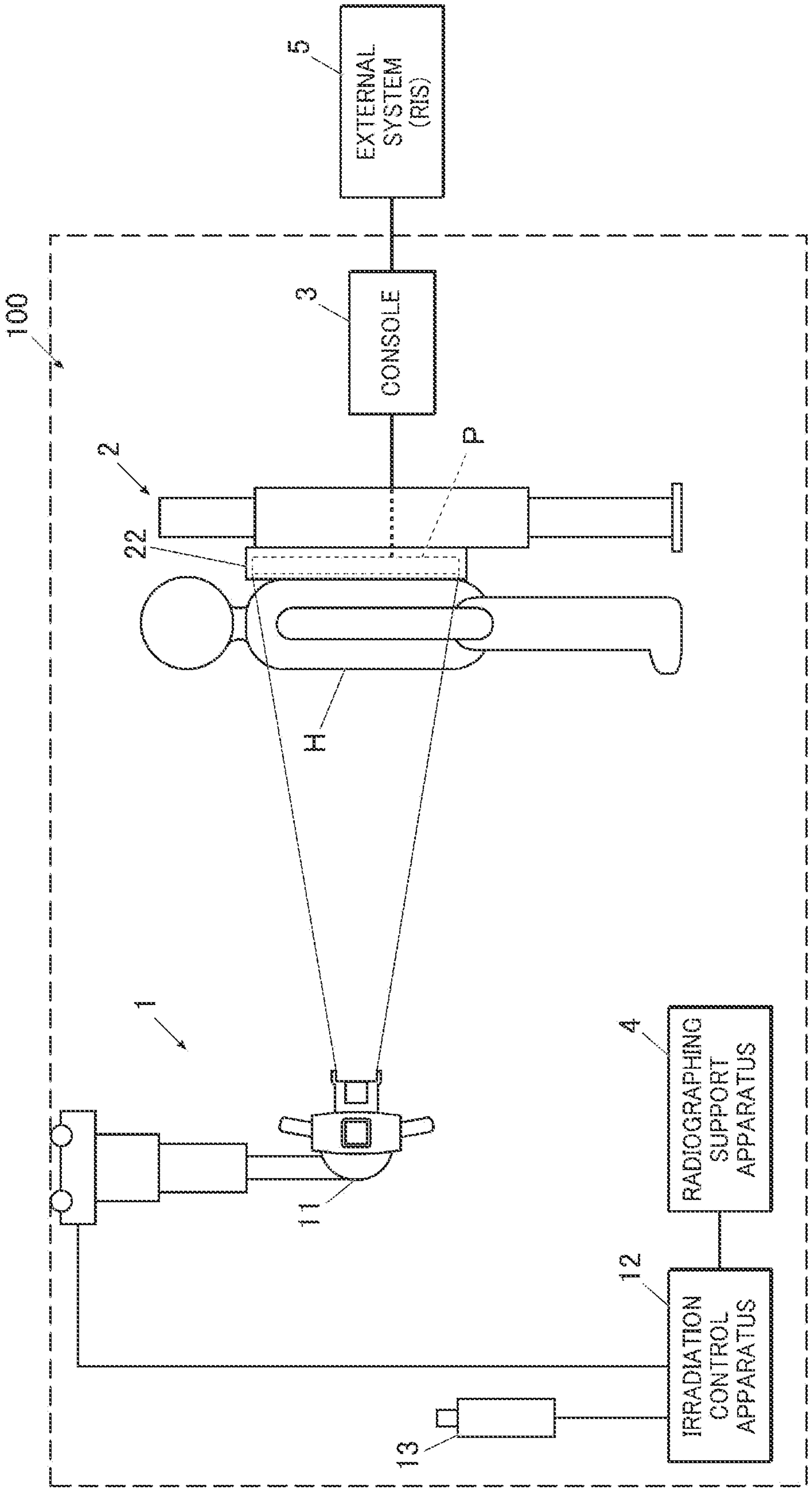
FIG. 10 is a view illustrating an overall configuration of a radiographic imaging support system in a third embodiment.

FIG. 10 illustrates a configuration of the radiographic imaging support system 100 of the third embodiment.

As illustrated in FIG. 10, in the third embodiment, the radiographing support apparatus 4 is connected to the radiation irradiation apparatus 1 so as to be able to transmit/receive data.

Figure 11:
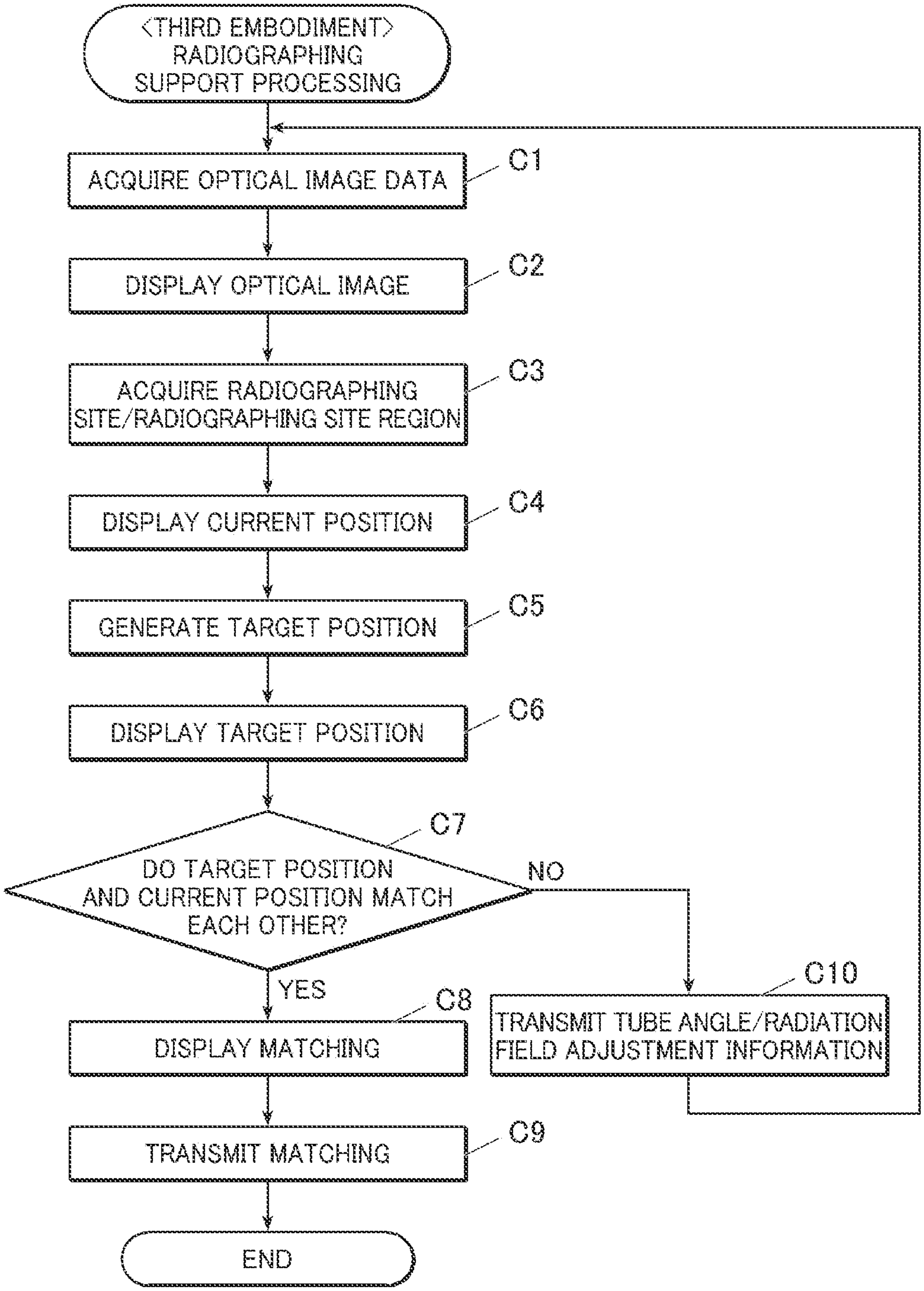
FIG. 11 is a flowchart indicating flow of radiographing support processing in the third embodiment.

FIG. 11 indicates a flowchart of the radiographing support processing in the third embodiment.

First, the controller 41 performs processing from step C1 to step C8 that is similar to the processing from step A1 to step A8 of the radiographing support processing in the first embodiment.

After step C8, the controller 41 transmits a notification indicating that the current position of the radiographing site matches the position appropriate for radiographic imaging, to the radiation irradiation apparatus 1 (step C9), and the present processing ends.

When the radiation irradiation apparatus 1 receives the notification indicating that the current position of the radiographing site matches the position appropriate for radiographic imaging from the radiographing support apparatus 4, the radiation irradiation apparatus 1 starts radiographic imaging through instruction operation by the operator.

Note that in a case where the radiation irradiation apparatus 1 includes a display, the controller 41 may transmit data for display for displaying matching of the outline of the current position of the radiographing site and the outline of the target position of the radiographing site in a distinguishable form to the radiation irradiation apparatus 1 in step C9. When the radiation irradiation apparatus 1 receives the data for display, the radiation irradiation apparatus 1 performs display on the display of the radiation irradiation apparatus 1 on the basis of the data for display.

On the other hand, in a case where the outline of the current position of the radiographing site does not match the outline of the target position of the radiographing site (step C7; NO), the controller 41 transmits information for adjusting a tube angle and a radiation field based on a difference between the outline of the current position of the radiographing site and the outline of the target position of the radiographing site to the radiation irradiation apparatus 1 (step C10) and returns the present processing to step C1. Then, the controller 41 repeatedly performs the processing from step C1 to step C7 and step C10 until the outlines match each other.

When the radiation irradiation apparatus 1 receives the information for adjusting the tube angle and the radiation field from the radiographing support apparatus 4, the radiation irradiation apparatus 1 changes the tube angle and the radiation field in the radiation source 11 by control by the irradiation control apparatus 12 on the basis of the information.

In this case, the outline of the current position of the radiographing site may be caused to match the outline of the target position of the radiographing site through adjustment of the tube angle and the radiation field without the operator or the subject H moving the radiographing site.

Fourth Embodiment

A fourth embodiment of the present invention will be described next. Points different from the first embodiment will be mainly described below.

A configuration of the radiographic imaging support system 100 in the fourth embodiment is similar to that in FIG. 1.

Further, the learned model 421 in the fourth embodiment outputs certainty of information to be output along with the radiographing site information, the radiographing site region information of the radiographing site, and the first target position information of the radiographing site if the image data of the optical image is input.

Further, the storage 42 in the fourth embodiment stores a template image for each radiographing site. Then, the controller 41 calculates similarity at the time of performing template matching using the template image.

Figure 12:
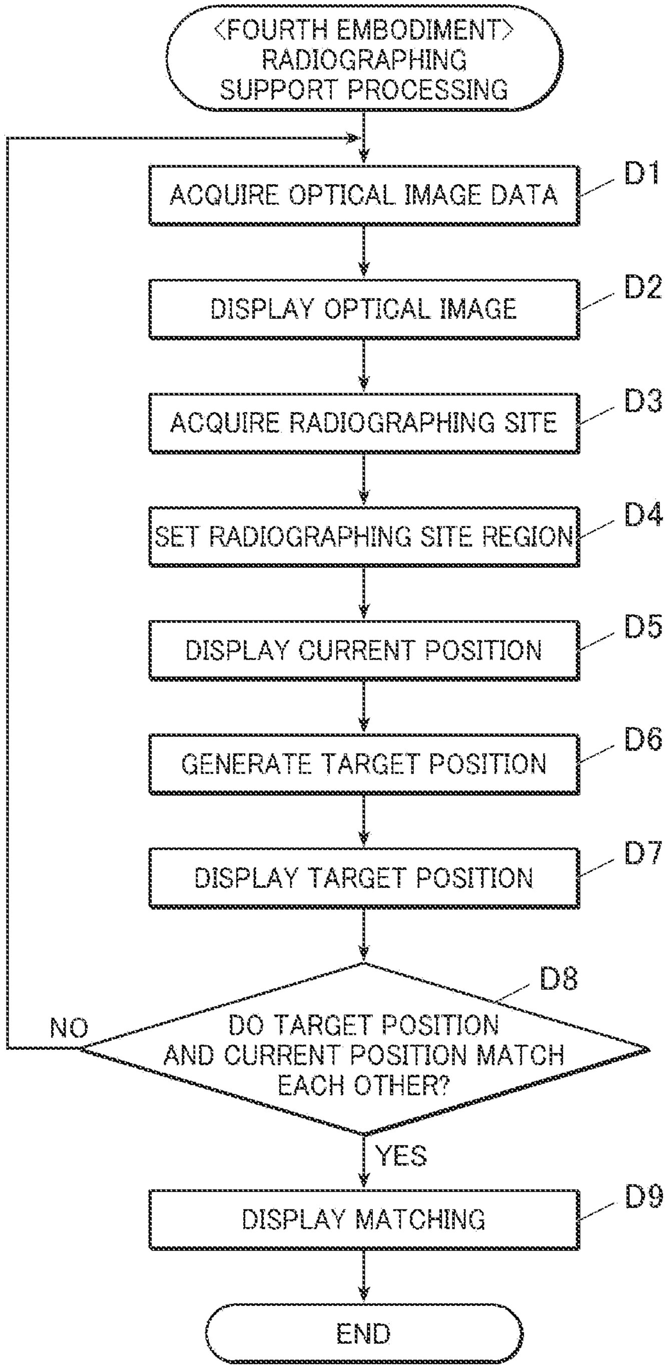
FIG. 12 is a flowchart indicating flow of radiographing support processing in a fourth embodiment.

FIG. 12 indicates a flowchart of radiographing support processing in the fourth embodiment.

First, the controller 41 performs processing in steps D1 and D2 that is similar to the processing in steps A1 and A2 of the radiographing support processing in the first embodiment.

Then, the controller 41 inputs the image data of the optical image acquired in step D1 to the learned model 421. Then, the controller 41 acquires radiographing site information of the subject H as output of the learned model 421 (step D3).

Then, the controller 41 sets the radiographing site region information so that certainty as output of the learned model 421 and similarity at the time of performing template matching using the template image corresponding to the radiographing site information acquired in step D3 become the highest (step D4).

Note that in step D4, the controller 41 may set the radiographing site region information using the following method. Specifically, the controller 41 acquires the radiographing site region information (first radiographing site region information) and the certainty as output of the learned model 421. Further, the controller 41 acquires the radiographing site region information (second radiographing site region information) and similarity by performing template matching using the template image corresponding to the radiographing site information acquired in step D3.

Then, the controller 41 compares the certainty and the similarity and sets radiographing site region information with higher accuracy between the first radiographing site region information and the second radiographing site region information as the radiographing site region information.

Then, the controller 41 performs processing from step D5 to step D9 that is similar to the processing from step A4 to step A8 of the radiographing support processing in the first embodiment.

Fifth Embodiment

A fifth embodiment of the present invention will be described next. Points different from the second embodiment will be mainly described below.

A configuration of the radiographic imaging support system 100 of the fifth embodiment is similar to that in FIG. 2.

Further, the learned model 421 in the fifth embodiment outputs certainty of information to be output along with the radiographing site information, the radiographing site region information of the radiographing site, and the first target position information of the radiographing site if the image data of the optical image is input, in a similar manner to the fourth embodiment.

Further, the storage 42 in the fifth embodiment stores a template image for each radiographing site in a similar manner to the fourth embodiment. Then, the controller 41 calculates similarity at the time of performing template matching using the template image.

Figure 13:
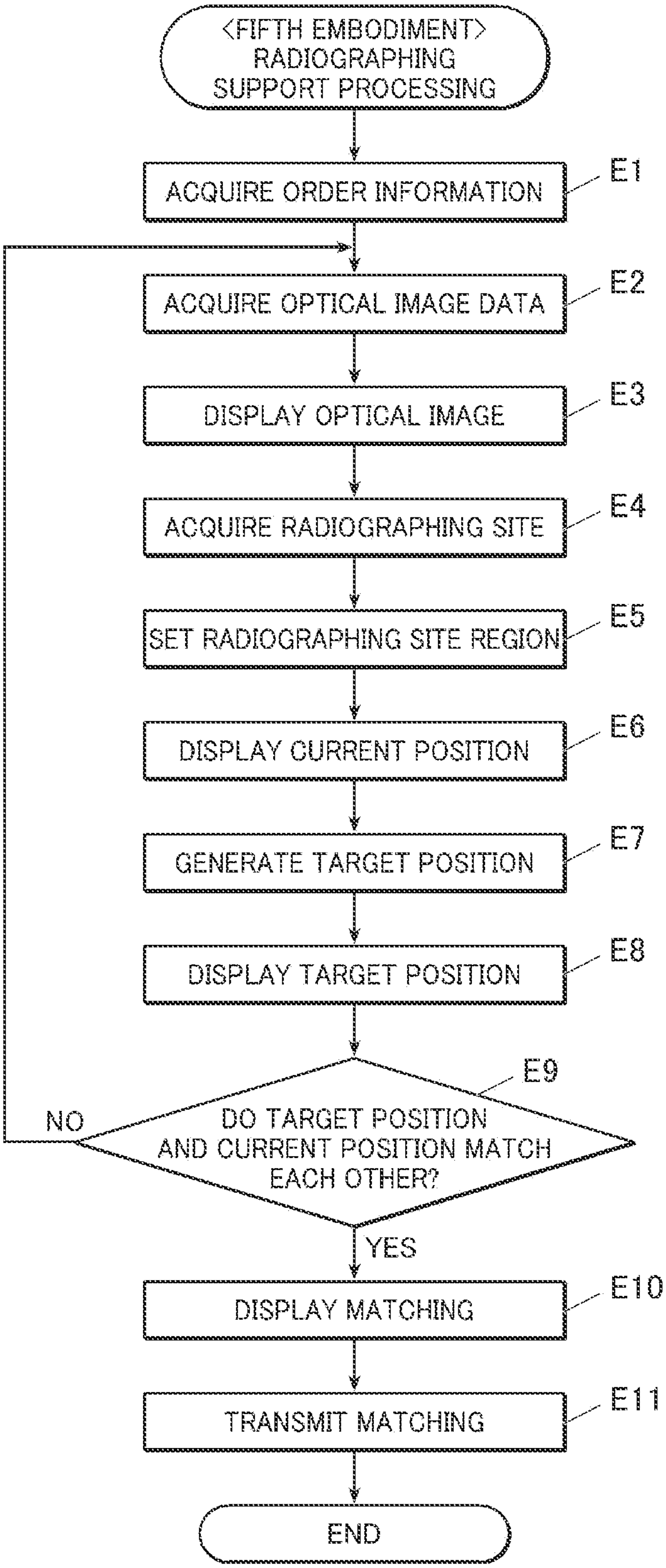
FIG. 13 is a flowchart indicating flow of radiographing support processing in a fifth embodiment.

FIG. 13 indicates a flowchart of radiographing support processing in the fifth embodiment.

First, the controller 41 performs processing from step E1 to step E3 that is similar to the processing from step B1 to step B3 of the radiographing support processing in the second embodiment.

Then, the controller 41 acquires the radiographing site information of the subject from the order information acquired in step E1 (step E4).

Then, the controller 41 inputs the image data of the optical image acquired in step E2 to the learned model 421. Then, the controller 41 sets the radiographing site region information so that the certainty as output of the learned model 421 and the similarity at the time of performing template matching using the template image corresponding to the radiographing site information acquired in step E4 become the highest (step E5).

Then, the controller 41 performs processing from step E6 to step E11 that is similar to the processing from step B5 to step B10 of the radiographing support processing in the second embodiment.

Note that in a case where the radiographing site information acquired in step E4 is not sufficient information (for example, in a case where the radiographing site information does not include information on the radiographing direction), the controller 41 may input the image data of the optical image to the learned model 421 and acquire the radiographing site information as output.

Sixth Embodiment

A sixth embodiment of the present invention will be described next. Points different from the first embodiment will be mainly described below.

A configuration of the radiographic imaging support system 100 of the sixth embodiment is similar to that in FIG. 1.

The storage 42 of the sixth embodiment stores a second threshold (predetermined second threshold) for each related site, to be used for determining whether the second target position information matches the second current position information on the basis of a difference between the second target position information and the second current position information in radiographing support processing of the sixth embodiment which will be described later.

Here, the related site, which is a site different from the radiographing site, indicates a site that enables a posture to be taken in which the radiographing site is disposed at an appropriate position with respect to an irradiation range of the radiation irradiation apparatus 1 by being disposed at a specific position.

For example, in a case where the radiographing site is inside of the left knee, a site such as the right leg that is a leg on an opposite side of the radiographing site and the pelvis (site that controls a direction of the left leg) becomes the related site.

These related sites are designated for each radiographing procedure, and thus, a plurality of related sites may be designated depending on radiographing procedure.

The second threshold is set at a relatively small value in a case where the related site is a fine site such as the finger, and is set at a relatively great value in a case where the related site is a large site such as the knee.

Further, the second threshold may be set for each radiographing procedure.

The learned model 421 of the sixth embodiment is a model that is caused to perform machine learning (deep learning) using the image data of the optical image captured with the optical camera 45, the first target position information (correct label) for each radiographing site corresponding to the image data and the second target position information (correct label) for each related site corresponding to the radiographing site.

The second target position information is information regarding the target position that is a position appropriate for radiographic imaging of the related site corresponding to the radiographing site of the subject H.

Then, if the image data of the optical image is input, the learned model 421 of the sixth embodiment performs inference and generates the radiographing site information indicating the radiographing site captured in the optical image, the radiographing site region information indicating a region of the radiographing site, the first target position information of the radiographing site, the related site information indicating the related site, the related site region information indicating a region of the related site, and the second target position information of the related site.

Figure 14:
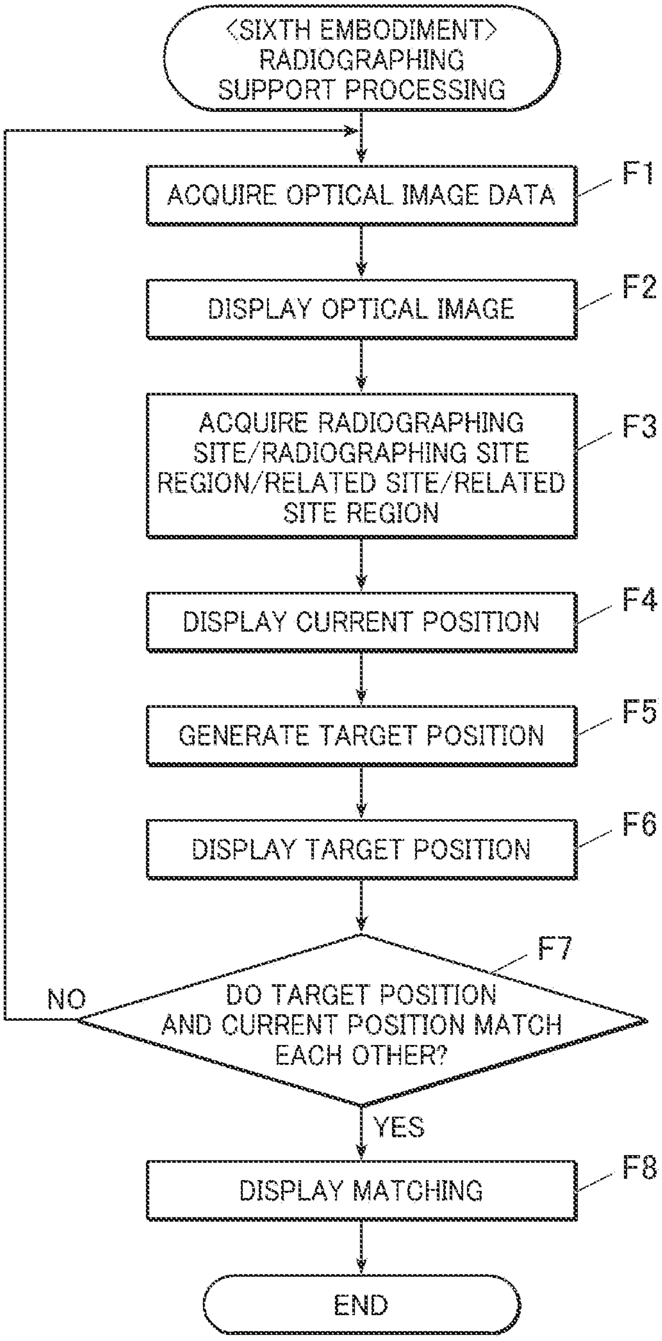
FIG. 14 is a flowchart indicating flow of radiographing support processing in a sixth embodiment.

FIG. 14 indicates a flowchart of radiographing support processing in the sixth embodiment.

First, the controller 41 performs processing in steps F1 and F2 that is similar to the processing in steps A1 and A2 of the radiographing support processing in the first embodiment.

Then, the controller 41 recognizes the radiographing site, the radiographing site region, the related site and the related site region of the subject on the basis of the image data of the optical image acquired in step F1.

Specifically, the controller 41 inputs the image data of the optical image acquired in step F1 to the learned model 421. Then, the controller 41 acquires the radiographing site information, the radiographing site region information, the related site information and the related site region information of the subject H as output of the learned model 421 (step F3).

Then, the controller 41 displays the outline of the radiographing site region acquired in step F3 as an outline of a current position of the radiographing site and displays the outline of the related site region as an outline of a current position of the related site in a superimposed manner on the optical image displayed in step F2 (step F4). The outline of the current position of the related site indicates a size of the related site.

Here, the outline of the current position of the related site is second current position information regarding a position of the related site corresponding to the radiographing site included in the image information.

Note that in step F4, the controller 41 may display the second current position information (the outline of the current position of the related site) along with the first current position information (the outline of the current position of the radiographing site) or may display only the second current position information without displaying the first current position information.

Then, the controller 41 generates the first target position information in a similar manner to step A5 of the radiographing support processing in the first embodiment. Then, the controller 41 acquires the second target position information corresponding to the related site information acquired in step F3 as output of the learned model 421. Then, the controller 41 generates the second target position information corresponding to the size of the related site by correcting the second target position information on the basis of the outline of the current position of the related site and the imaging direction of the optical camera 45 (step F5). In other words, the controller 41 generates the second target position information regarding the target position of the related site corresponding to the radiographing site using the image information based on the optical image acquired by the acquirer as input using the learned model 421 (learned classifier). Here, the controller 41 functions as a generator. Further, the second target position information includes information corresponding to a size of the related site corresponding to the radiographing site (information corresponding to the outline of the current position of the related site). The step F5 is a generation process.

Then, the controller 41 displays the first target position information corresponding to the size of the radiographing site generated in step F5 as an outline of the target position of the radiographing site in a superimposed manner on the optical image displayed in step F2. Then, the controller 41 displays the second target position information corresponding to the size of the related site generated in step F5 as an outline of the target position of the related site in a superimposed manner on the optical image displayed in step F2 (step F6). In other words, the controller 41 outputs the second target position information generated by the generator. Here, the controller 41 functions as an output device. The step F6 is an output process.

Note that in step F6, the controller 41 may display the second target position information (the outline of the target position of the related site) along with the first target position information (the outline of the target position of the radiographing site) or may display only the second target position information without displaying the first target position information.

Further, in steps F4 and F6, the controller 41 may display only the second current position information and the second target position information without displaying the first current position information and the first target position information.

Further, in steps F4 and F6, the first current position information, the first target position information, the second current position information, and the second target position information are preferably displayed in different aspects in color of line, line type, shape, and the like, of each outline so as to enable the operator or the subject H to easily distinguish the respective kinds of information.

Note that in a case where a plurality of pieces of related site information indicating the related site corresponding to the radiographing site are acquired in step F3, the controller 41 displays the second current position information corresponding to the respective pieces of the related site information and the second target position information in different aspects in color of line, line type, shape, and the like, of each outline so as to be easily distinguished.

Then, the controller 41 determines whether or not the outline of the current position of the radiographing site (first current position information) displayed in step F4 matches the outline of the target position of the radiographing site (first target position information) displayed in step F6 in a similar manner to step A7 of the radiographing support processing in the first embodiment.

Then, the controller 41 determines whether or not the outline of the current position of the related site (second current position information) displayed in step F4 matches the outline of the target position of the related site (second target position information) displayed in step F6 (step F7).

Specifically, the controller 41 acquires a second threshold corresponding to the related site information acquired from the storage 42 in step F3. Then, in a case where a difference between the outline of the current position of the related site and the outline of the target position of the related site is within the second threshold, the controller 41 determines that the outline of the current position of the related site matches the outline of the target position of the related site. In other words, in a case where a difference between the second target position information and the second current position information is within the second threshold, the controller 41 determines that the second target position information matches the second current position information. Here, the controller 41 functions as a determiner.

Note that in a case where only the second current position information and the second target position information are displayed without displaying the first current position information and the first target position information in steps F4 and F6, the controller 41 may perform the following processing in step F7. The processing is determining whether or not the second current position information matches the second target position information without determining whether or not the first current position information matches the first target position information.

However, the first target position information is interrelated with the second target position information. Thus, even in a case where the second current position information matches the second target position information, in a case where an optimal radiographing posture is desired, it is necessary that the first current position information matches the first target position information. Thus, in step F7, the controller 41 preferably determines whether or not the first current position information matches the first target position information and determines whether or not the second current position information matches the second target position information.

In a case where the outline of the current position of the radiographing site matches the outline of the target position of the radiographing site, and the outline of the current position of the related site matches the outline of the target position of the related site (step F7; YES), the controller 41 displays matching in a distinguishable form (step F8), and the present processing ends.

This enables the operator or the subject H to recognize that the current position of the radiographing site matches the position (target position) appropriate for radiographic imaging.

When the operator recognizes that the current position of the radiographing site matches the position appropriate for radiographic imaging, the operator starts radiographic imaging in the radiographic imaging apparatus.

Note that in a case where the controller 41 only determines whether or not the second current position information matches the second target position information without determining whether or not the first current position information matches the first target position information in step F7, the controller 41 may perform the following processing. The processing is that, in a case where the outline of the current position of the related site matches the outline of the target position of the related site (step F7; YES), the controller 41 displays matching in a distinguishable form (step F8), and the present processing ends.

On the other hand, in a case where the outline of the current position of the radiographing site does not match the outline of the target position of the radiographing site or the outline of the current position of the related site does not match the outline of the target position of the related site (step F7; NO), the controller 41 returns the present processing to step F1. Then, the controller 41 repeatedly performs the processing from step F1 to step F7 until the outlines match each other.

Note that in a case where the controller 41 only determines whether or not the second current position information matches the second target position information without determining whether or not the first current position information matches the first target position information in step F7, the controller 41 may perform the following processing. The processing is that in a case where the outline of the current position of the related site does not match the outline of the target position of the related site (step F7; NO), the controller 41 returns the present processing to step F1.

The operator or the subject H moves the radiographing site and the related site so that the outline of the current position of the radiographing site displayed on the display 44 matches the outline of the target position of the radiographing site, and the outline of the current position of the related site matches the outline of the target position of the related site.

Seventh Embodiment

A seventh embodiment of the present invention will be described next. Points different from the second embodiment will be mainly described below.

A configuration of the radiographic imaging support system 100 in the seventh embodiment is similar to that in FIG. 8.

The storage 42 in the seventh embodiment stores the related site information indicating the related site corresponding to the radiographing site.

Further, the storage 42 stores a template image for each radiographing site and a template image for each related site corresponding to the radiographing site.

Further, the storage 42 stores the first reference position information and second reference position information regarding the position of the related site corresponding to the radiographing position of the radiographing site.

Further, the storage 42 stores the second threshold (predetermined second threshold) for each related site in a similar manner to the sixth embodiment.

Figure 15:
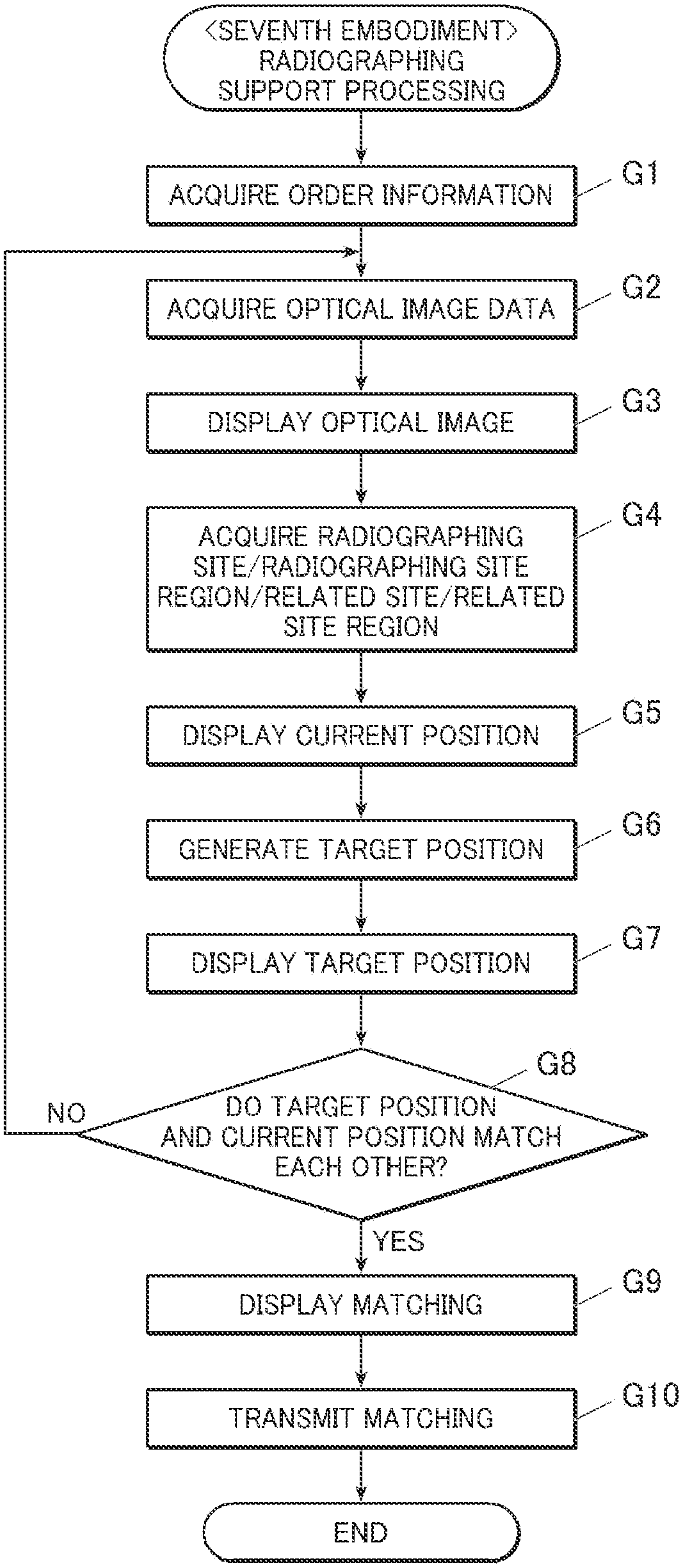
FIG. 15 is a flowchart indicating flow of radiographing support processing in a seventh embodiment.

FIG. 15 indicates a flowchart of radiographing support processing in the seventh embodiment.

First, the controller 41 performs processing from step G1 to step G3 that is similar to the processing from step B1 to step B3 of the radiographing support processing in the second embodiment.

Then, the controller 41 acquires the radiographing site information of the subject from the order information acquired in step G1.

Then, the controller 41 acquires the related site information on the basis of the radiographing site from the storage 42. Note that the controller 41 may acquire the related site information on the basis of the radiographing conditions, and the like, included in the order information acquired in step G1. For example, in a case where the radiographing conditions are radiographing on a side surface of the knee joint, "pelvis+side not to be examined (leg)" is set as the related site.

Then, the controller 41 acquires the template image corresponding to the radiographing site information acquired from the order information, from the storage 42.

Then, the controller 41 recognizes (acquires) the radiographing site region in the image data of the optical image acquired in step G2 by performing template matching using the template image corresponding to the radiographing site information.

Then, the controller 41 acquires the template image corresponding to the related site information acquired from the storage 42, from the storage 42.

Then, the controller 41 recognizes (acquires) the related site region in the image data of the optical image acquired in step G2 by performing template matching using the template image corresponding to the related site information (step G4).

Then, the controller 41 performs processing in step G5 that is similar to the processing in step F4 in the radiographing support processing in the sixth embodiment.

Then, the controller 41 generates the first target position information corresponding to the size of the radiographing site in a similar manner to step B6 of the radiographing support processing in the second embodiment.

Then, the controller 41 acquires the second reference position information corresponding to the related site information acquired in step G4, from the storage 42.

Then, the controller 41 generates the second target position information corresponding to the size of the related site by correcting the second reference position information on the basis of the outline of the current position of the related site and the imaging direction of the optical camera 45 (step G6). In other words, the controller 41 generates the second target position information regarding the target position of the related site corresponding to the radiographing site on the basis of the second reference position information regarding the position of the related site corresponding to the radiographing position of the radiographing site and the image information acquired by the acquirer. Here, the controller 41 functions as a generator. Further, the second target position information includes information corresponding to the size of the related site corresponding to the radiographing site (information corresponding to the outline of the related site corresponding to the radiographing site). The step G6 is a generation process.

Then, the controller 41 performs processing from step G7 to step G9 that is similar to the processing from step F6 to step F8 of the radiographing support processing in the sixth embodiment.

Then, the controller 41 performs processing in step G10 that is similar to the processing in step B10 of the radiographing support processing in the second embodiment.

Note that description in the above-described embodiments is one preferred example of the present invention, and the present invention is not limited to this.

For example, the radiographic imaging support system 100 may include an examination apparatus that acquires electrocardiogram, oxygen concentration, and the like, an eye tracker that is worn by the operator (such as a radiographer) and detects a line of sight of the operator, and the like, as the external system 5 in place of RIS.

In this case, the controller 41 acquires the radiographing site information, the radiographing site region information, the related site information and the related site region information while taking into account information output from the examination apparatus, the eye tracker, and the like, in the radiographing support processing.

For example, in a case where the radiographic imaging support system 100 includes an eye tracker, the related site is specified with a viewpoint that on which related site an experienced operator focuses attention (or how the experienced operator moves) to position the subject at an appropriate radiographing position.

Specifically, in a case where a heat map can be acquired as information to be output from the eye tracker, the controller 41 acquires the related site information on the basis of a period during which a line of sight of the operator is focused on a specific region.

Further, in a case where a gaze plot can be acquired as information to be output from the eye tracker, the controller 41 acquires a plurality of pieces of related site information on the basis of movement of the line of sight of the operator and movement order.

Further, the controller 41 may acquire the related site information on the basis of information to be output from the eye tracker and correct the first current position information and/or the first target position information so as to take into account balance of the related site and the radiographing site on the basis of the related site information.

Further, in a case where the related site information and the related site region information cannot be acquired in the radiographing support processing in the above-described sixth embodiment and seventh embodiment, the controller 41 may not display the second current position information and the second target position information. Further, in this case, the controller 41 may only determine whether or not the first current position information matches the first target position information without determining whether or not the second current position information matches the second target position information.

Effects

According to the above-described embodiments, the radiographic imaging support system 100 of the present invention is a radiographic imaging support system that supports positioning of a radiographing site of a subject H with respect to a radiographic imaging apparatus (the radiation irradiation apparatus 1 and the radiation detection apparatus 2), the radiographic imaging support system includes an acquirer (controller 41) that acquires image information (image data of an optical image) based on an optical image obtained by capturing an image of the radiographing site with the optical camera 45, a generator (controller 41) that generates first target position information regarding a target position of the radiographing site using the image information acquired by the acquirer as input using a learned classifier (learned model 421), and an output device (controller 41) that outputs the first target position information generated by the generator, and the first target position information includes information corresponding to a size of the radiographing site.

This enables an operator (such as a radiographer) of the radiographic imaging apparatus or the subject H to move the radiographing site of the subject while recognizing the first target position information corresponding to the size of the radiographing site. It is therefore possible to easily position the radiographing position of the subject at an appropriate radiographing position.

Further, the radiographic imaging support system 100 is a radiographic imaging support system that supports positioning of a radiographing site of a subject H with respect to a radiographic imaging apparatus (the radiation irradiation apparatus 1 and the radiation detection apparatus 2), the radiographic imaging support system 100 includes an acquirer (controller 41) that acquires image information (image data of an optical image) based on an optical image obtained by capturing an image of the radiographing site with the optical camera 45 and a generator (controller 41) that generates first target position information regarding a target position of the radiographing site on the basis of the first reference position information regarding the radiographing position of the radiographing site and the image information acquired by the acquirer, and an output device (controller 41) that outputs the first target position information generated by the generator, and the first target position information includes information corresponding to a size of the radiographing site.

This enables the operator (such as a radiographer) of the radiographic imaging apparatus or the subject H to move the radiographing site of the subject while recognizing the first target position information corresponding to the size of the radiographing site. It is therefore possible to easily position the radiographing position of the subject at an appropriate radiographing position.

Further, in the radiographic imaging support system 100, the first target position information includes information regarding an outline of the radiographing site.

This enables the operator (such as a radiographer) of the radiographic imaging apparatus or the subject H to recognize an outline of the target position of the radiographing site. It is therefore possible to easily position the radiographing position of the subject at an appropriate radiographing position.

Further, in the radiographic imaging support system 100, the first target position information is based on an imaging direction of the optical camera 45.

It is therefore possible to generate more accurate first target position information based on the imaging direction of the optical camera 45.

Further, in the radiographic imaging support system 100, the output device outputs an optical image including the radiation detection apparatus 2 provided in the radiographic imaging apparatus and outputs the optical image so that the first target position information is located on at least part of the radiation detection apparatus 2 in the optical image.

It is therefore possible to position the radiographing position of the subject at an appropriate radiographing position on the radiation detector P of the radiation detection apparatus 2.

Further, in the radiographic imaging support system 100, the output device outputs the first target position information and first current position information regarding a position of the radiographing site included in the image information, in a distinguishable form.

This enables the operator (such as a radiographer) of the radiographic imaging apparatus or the subject H to easily recognize a difference between a target position of the radiographing site and a current position of the radiographing site.

Further, the radiographic imaging support system 100 includes a determiner (controller 41) that determines that the first target position information matches the first current position information in a case where a difference between the first target position information and the first current position information is within a predetermined first threshold, and the predetermined first threshold is set for each of the radiographing site.

Thus, for example, the first threshold can be set at a threshold appropriate for the radiographing site such that the first threshold is set at a relatively small value in a case where the radiographing site is a fine site such as the finger, and the first threshold is set at a relatively great value in a case where the radiographing site is a large site such as the knee.

Further, the radiographic imaging support system 100 includes a determiner (controller 41) that determines that the first target position information matches the first current position information in a case where a difference between the first target position information and the first current position information is within the predetermined first threshold, and in a case where it is determined by the determiner that the first target position information matches the first current position information, the output device outputs matching in a distinguishable form.

This enables the operator (such as a radiographer) of the radiographic imaging apparatus or the subject H to easily recognize that the current position of the radiographing site matches a position (target position) appropriate for radiographic imaging.

Further, the radiographic imaging support system 100 is a radiographic imaging support system that supports positioning of a radiographing site of a subject H with respect to a radiographic imaging apparatus (the radiation irradiation apparatus 1 and the radiation detection apparatus 2), and the radiographic imaging support system 100 includes an acquirer (controller 41) that acquires image information (image data of an optical image) based on an optical image obtained by capturing an image of the radiographing site with the optical camera 45, a generator (controller 41) that generates second target position information regarding a target position of a related site corresponding to the radiographing site using the image information acquired by the acquirer as input using a learned classifier (learned model 421), and an output device (controller 41) that outputs the second target position information generated by the generator.

This enables the operator (such as a radiographer) of the radiographic imaging apparatus or the subject H to move the related site of the subject while recognizing the second target position information regarding the target position of the related site corresponding to the radiographing site. It is therefore possible to easily position the radiographing position of the subject at an appropriate radiographing position.

Further, the radiographic imaging support system 100 is a radiographic imaging support system that supports positioning of a radiographing site of a subject H with respect to a radiographic imaging apparatus (the radiation irradiation apparatus 1 and the radiation detection apparatus 2), and the radiographic imaging support system 100 includes an acquirer (controller 41) that acquires image information (image data of an optical image) based on an optical image obtained by capturing an image of the radiographing site with the optical camera 45, a generator (controller 41) that generates second target position information regarding a target position of a related site corresponding to the radiographing site on the basis of second reference position information regarding a position of the related site corresponding to a radiographing position of the radiographing site and the image information acquired by the acquirer, and an output device (controller 41) that outputs the second target position information generated by the generator.

This enables the operator (such as a radiographer) of the radiographic imaging apparatus or the subject H to move the related site of the subject while recognizing the second target position information regarding the target position of the related site corresponding to the radiographing site. It is therefore possible to easily position the radiographing position of the subject at an appropriate radiographing position.

Further, in the radiographic imaging support system 100, the second target position information includes information corresponding to a size of the related site corresponding to the radiographing site.

This enables the operator (such as a radiographer) of the radiographic imaging apparatus or the subject H to move the related site of the subject while recognizing the second target position information corresponding to the size of the related site. It is therefore possible to easily position the radiographing position of the subject at an appropriate radiographing position.

Further, in the radiographic imaging support system 100, the second target position information includes information regarding an outline of the related site corresponding to the radiographing site.

This enables the operator (such as a radiographer) of the radiographic imaging apparatus or the subject H to recognize the outline of the target position of the related site. It is therefore possible to easily position the radiographing position of the subject at an appropriate radiographing position.

Further, in the radiographic imaging support system 100, the output device outputs the second target position information and second current position information regarding a position of the related site corresponding to the radiographing site included in the image information, in a distinguishable form.

This enables the operator (such as a radiographer) of the radiographic imaging apparatus or the subject H to easily recognize a difference between the target position of the related site and the current position of the related site.

Further, the radiographic imaging support system 100 includes a determiner that determines that the second target position information matches the second current position information in a case where a difference between the second target position information and the second current position information is within a predetermined second threshold, and the predetermined second threshold is set for each of the related site corresponding to the radiographing site.

Thus, for example, the second threshold can be set at a threshold appropriate for the related site such that the second threshold is set at a relatively small value in a case where the related site is a fine site such as the finger and the second threshold is set at a relatively great value in a case where the related site is a large site such as the knee.

Further, in the radiographic imaging support system 100, the determiner determines that first target position information matches first current position information in a case where a difference between the first target position information regarding a target position of the radiographing site and the first current position information regarding a position of the radiographing site included in the image information is within a predetermined first threshold, and determines whether the second target position information matches the second current position information.

Thus, by determining that the first target position information matches the first current position information and that the second target position information matches the second current position information, it is possible to position the radiographing position of the subject at a more accurate radiographing position.

While the first to the seventh embodiments have been described above, the description in the above-described embodiments is a preferred example of the present invention, and the present invention is not limited to this.

For example, while in the above-described embodiments, the controller 41 of the radiographing support apparatus 4 functions as the acquirer, the generator, the output device and the determiner, the configuration is not limited to this. The controller 31 of the console 3 or a controller provided in an external apparatus (such as, for example, a cloud computer) capable of performing communication with the radiographic imaging support system 100 may function as the acquirer, the generator, the output device and the determiner.

Further, for example, while an example has been disclosed in the above description where a hard disk, a non-volatile memory of a semiconductor, or the like, is used as a computer-readable medium of the program according to the present invention, the present invention is not limited to this example. As another computer-readable medium, a portable recording medium, such as a CD-ROM, may be applied. Carrier waves are also applicable as a medium that provides data on the program according to the present invention via a communication line.

Detailed configurations and detailed operation of the respective apparatuses that constitute the radiographic imaging support system can be changed as appropriate within a range not deviating from the gist of the present invention.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A radiographic imaging support system that supports positioning of a radiographing site of a subject with respect to a radiographic imaging apparatus, the radiographic imaging support system comprising:

a hardware processor that acquires image information based on an optical image obtained by capturing an image of the radiographing site with an optical camera, generates first target position information regarding a target position of the radiographing site based on first current position information regarding a position of the radiographing site, and outputs the generated first target position information, wherein the first target position information is position information for positioning the radiographing site, wherein the first target position information includes information corresponding to a size of the radiographing site, wherein the hardware processor generates the first target position information regarding the target position of the radiographing site on a basis of first reference position information regarding a radiographing position of the radiographing site and the image information acquired, and wherein the hardware processor generates first target position information regarding the target position of the radiographing site by correcting the first reference position information based on the first current position information.

2. The radiographic imaging support system according to claim 1, wherein the hardware processor generates first target position information regarding the target position of the radiographing site using the image information acquired as input using a learned classifier.

3. The radiographic imaging support system according to claim 1, wherein the first target position information includes information regarding an outline of the radiographing site.

4. The radiographic imaging support system according to claim 1, wherein the first target position information is based on an imaging direction of the optical camera.

5. The radiographic imaging support system according to claim 1, wherein the hardware processor outputs the optical image including a radiation detection apparatus provided in the radiographic imaging apparatus and outputs the optical image so that the first target position information is located on at least part of the radiation detection apparatus in the optical image.

6. The radiographic imaging support system according to claim 1, wherein the hardware processor outputs the first target position information and the first current position information included in the image information, in a distinguishable form.

7. The radiographic imaging support system according to claim 6, wherein the hardware processor determines that the first target position information matches the first current position information in a case where a difference between the first target position information and the first current position information is within a predetermined first threshold, and the predetermined first threshold is set for each of the radiographing site.

8. The radiographic imaging support system according to claim 6, wherein the hardware processor determines that the first target position information matches the first current position information in a case where a difference between the first target position information and the first current position information is within a predetermined first threshold, and in a case where it is determined that the first target position information matches the first current position information, the hardware processor outputs matching in a distinguishable form.

9. The radiographic imaging support system according to claim 1, wherein the first target position information is generated to indicate an appropriate radiographing position of the radiographing site with respect to the radiographic imaging apparatus based on the optical image of the radiographing site, whereby the subject can be positioned at the appropriate radiography position.

10. A radiographic imaging support method for supporting positioning of a radiographing site of a subject with respect to a radiographic imaging apparatus, the radiographic imaging support method comprising:

by a hardware processor, acquiring image information based on an optical image obtained by capturing an image of the radiographing site with an optical camera;

generating first target position information regarding a target position of the radiographing site based on first current position information regarding a position of the radiographing site; and outputting the generated first target position information, wherein the first target position information is position information for positioning the radiographing site, wherein the first target position information includes information corresponding to a size of the radiographing site, wherein the first target position information regarding the target position of the radiographing site is generated on a basis of first reference position information regarding a radiographing position of the radiographing site and the image information acquired, and wherein the first target position information regarding the target position of the radiographing site is generated by correcting the first reference position information based on the first current position information.

11. A non-transitory computer-readable recording medium storing a program for causing a computer of a radiographic imaging support system that supports positioning of a radiographing site of a subject with respect to a radiographic imaging apparatus to:

acquire image information based on an optical image obtained by capturing an image of the radiographing site with an optical camera;

generate first target position information regarding a target position of the radiographing site based on first current position information regarding a position of the radiographing site; and output the generated first target position information, wherein the first target position information is position information for positioning the radiographing site, wherein the first target position information includes information corresponding to a size of the radiographing site, wherein the first target position information regarding the target position of the radiographing site is generated on a basis of first reference position information regarding a radiographing position of the radiographing site and the image information acquired, and wherein the first target position information regarding the target position of the radiographing site is generated by correcting the first reference position information based on the first current position information.

* * * * *